(12) United States Patent
Friedman et al.

(10) Patent No.: US 9,702,762 B2
(45) Date of Patent: Jul. 11, 2017

(54) CALIBRATION AND IMAGE PROCESSING DEVICES, METHODS, AND SYSTEMS

(71) Applicant: LightLab Imaging, Inc., Westford, MA (US)

(72) Inventors: Joel M. Friedman, Andover, MA (US); Amr Elbasiony, Chelmsford, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 786 days.

(21) Appl. No.: 13/842,712

(22) Filed: Mar. 15, 2013

(65) Prior Publication Data
US 2014/0268167 A1    Sep. 18, 2014

(51) Int. Cl.
| | |
|---|---|
| G06K 9/00 | (2006.01) |
| A61B 8/14 | (2006.01) |
| G01J 9/02 | (2006.01) |
| G06T 7/00 | (2017.01) |
| A61B 8/12 | (2006.01) |
| G06T 7/12 | (2017.01) |

(52) U.S. Cl.
CPC ........ *G01J 9/02* (2013.01); *A61B 8/12* (2013.01); *G06T 7/0012* (2013.01); *G06T 7/12* (2017.01); *G06T 2207/10101* (2013.01); *G06T 2207/20168* (2013.01)

(58) Field of Classification Search
None
See application file for complete search history.

(56) References Cited

U.S. PATENT DOCUMENTS

| | | |
|---|---|---|
| 4,548,473 A | 10/1985 | Lo et al. |
| 5,321,501 A | 6/1994 | Swanson et al. |
| 5,459,570 A | 10/1995 | Swanson et al. |
| 5,465,147 A | 11/1995 | Swanson |
| 5,509,093 A | 4/1996 | Miller et al. |
| 5,518,810 A | 5/1996 | Nishihara et al. |
| 5,619,368 A | 4/1997 | Swanson |

(Continued)

FOREIGN PATENT DOCUMENTS

JP    63-127201    5/1988

OTHER PUBLICATIONS

Written Opinion of the International Searching Authority, International Application No. PCT/US2008/012701, mailed on May 14, 2009 (10 pgs.).

(Continued)

*Primary Examiner* — Matthew Bella
*Assistant Examiner* — Jose M Torres
(74) *Attorney, Agent, or Firm* — K&L Gates LLP

(57) ABSTRACT

In part, the invention relates to systems and methods of calibrating a plurality of frames generated with respect to a blood vessel as a result of a pullback of an intravascular imaging probe being pullback through the vessel. A calibration feature disposed in the frames that changes between a subset of the frames can be used to perform calibration. Calibration can be performed post-pullback. Various filters and image processing techniques can be used to identify one or more feature in the frames including, without limitation, a calibration feature, a guidewire, a side branch, a stent strut, a lumen of the blood vessel, and other features. The feature can be displayed using a graphic user interface.

11 Claims, 17 Drawing Sheets

(56) References Cited

U.S. PATENT DOCUMENTS

| | | |
|---|---|---|
| 5,632,767 A | 5/1997 | Sinofsky |
| 5,643,253 A | 7/1997 | Baxter et al. |
| 5,748,598 A | 5/1998 | Swanson et al. |
| 5,784,352 A | 7/1998 | Swanson et al. |
| 5,908,415 A | 6/1999 | Sinofsky |
| 5,947,959 A | 9/1999 | Sinofsky |
| 5,956,355 A | 9/1999 | Swanson et al. |
| 6,111,645 A | 8/2000 | Tearney et al. |
| 6,134,003 A | 10/2000 | Tearney et al. |
| 6,160,826 A | 12/2000 | Swanson et al. |
| 6,191,862 B1 | 2/2001 | Swanson et al. |
| 6,270,492 B1 | 8/2001 | Sinofsky |
| 6,282,011 B1 | 8/2001 | Tearney et al. |
| 6,348,960 B1 | 2/2002 | Etori et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,692,824 B2 | 2/2004 | Benz et al. |
| 6,706,004 B2 | 3/2004 | Tearney et al. |
| 6,718,089 B2 | 4/2004 | James et al. |
| 6,760,112 B2 | 7/2004 | Reed et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,942,657 B2 | 9/2005 | Sinofsky et al. |
| 6,974,557 B1 | 12/2005 | Webler et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,355,699 B2 | 4/2008 | Gilbert et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,492,522 B2 | 2/2009 | Gilbert et al. |
| 7,576,861 B2 | 8/2009 | Gilbert et al. |
| 7,625,366 B2 | 12/2009 | Atlas |
| 7,711,413 B2 | 5/2010 | Feldman et al. |
| 7,783,337 B2 | 8/2010 | Feldman et al. |
| 7,813,609 B2 | 10/2010 | Petersen et al. |
| 7,848,791 B2 | 12/2010 | Schmitt et al. |
| 7,853,316 B2 | 12/2010 | Milner et al. |
| 7,916,387 B2 | 3/2011 | Schmitt et al. |
| 7,935,060 B2 | 5/2011 | Schmitt et al. |
| 7,967,743 B2 | 6/2011 | Ishihara |
| 8,358,461 B2 | 1/2013 | Huber et al. |
| 2002/0161351 A1 | 10/2002 | Samson et al. |
| 2005/0201662 A1 | 9/2005 | Petersen et al. |
| 2006/0095065 A1 | 5/2006 | Tanimura et al. |
| 2006/0264743 A1* | 11/2006 | Kleen .................. A61B 5/0066 600/425 |
| 2007/0161893 A1 | 7/2007 | Milner et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0190586 A1 | 8/2011 | Kemp |
| 2011/0216325 A1 | 9/2011 | Schmitt |
| 2011/0228280 A1 | 9/2011 | Schmitt et al. |
| 2011/0230758 A1* | 9/2011 | Eichler ................ A61B 5/06 600/424 |
| 2012/0057157 A1 | 3/2012 | Petersen et al. |
| 2012/0075638 A1* | 3/2012 | Rollins .............. A61B 1/00009 356/479 |
| 2012/0162660 A1 | 6/2012 | Kemp |
| 2012/0224751 A1 | 9/2012 | Kemp et al. |
| 2012/0236883 A1 | 9/2012 | Adler |
| 2012/0238869 A1 | 9/2012 | Schmitt et al. |
| 2012/0250028 A1 | 10/2012 | Schmitt et al. |
| 2012/0310081 A1 | 12/2012 | Adler et al. |
| 2013/0006105 A1* | 1/2013 | Furuichi .............. A61B 5/0066 600/427 |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2014/0270445 A1* | 9/2014 | Kemp ................. A61B 5/6852 382/131 |

OTHER PUBLICATIONS

International Search Report, International Application No. PCT/US2008/012701, mailed on May 14, 2009 (7 pgs.).

PCT International Preliminary Report on Patentability for International Application No. PCT/US2008/12701, issued May 18, 2010 (10 pgs.).

Annex to Form PCT/ISA206 Communication Relating to the Results of the Partial International Search for International Application No. PCT/US2008/012701, mailed on Feb. 27, 2009 (3 pgs.).

PCT International Search Report and Written Opinion of International Searching Authority for International Application No. PCT/US2013/078500, mailed on Jul. 8, 2014 (14 pgs.).

Tung et al., "Automatic Detection of Coronary Stent Struts in Intravascular OCT Imaging," Proceedings of SPIE, vol. 8315, Feb. 22, 2012 (8 pgs.).

* cited by examiner

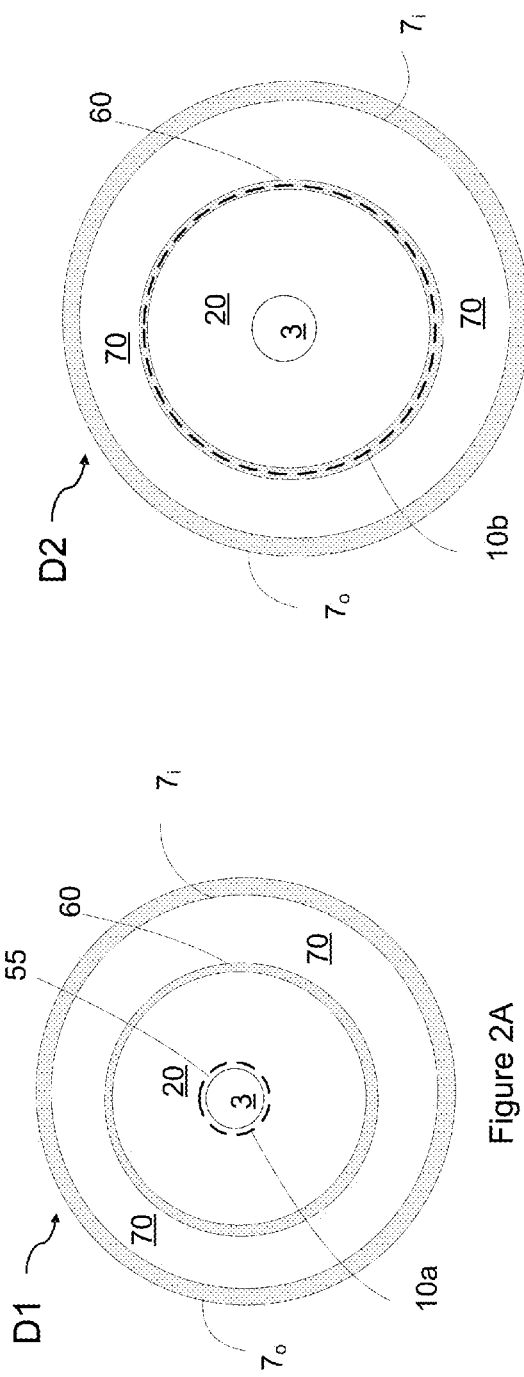
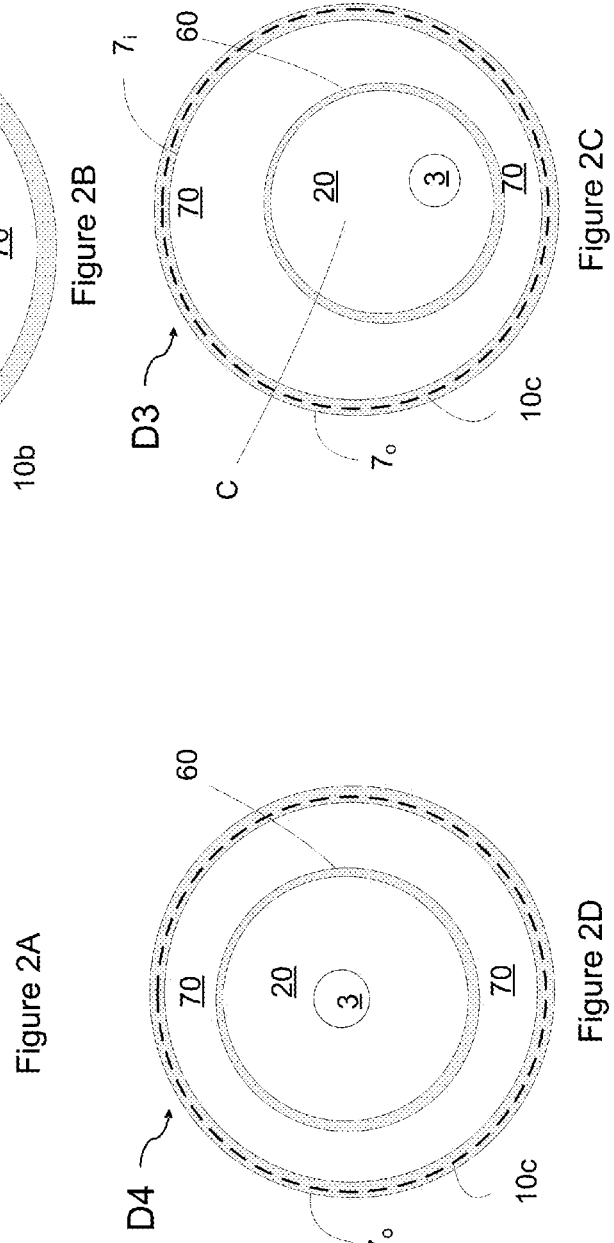

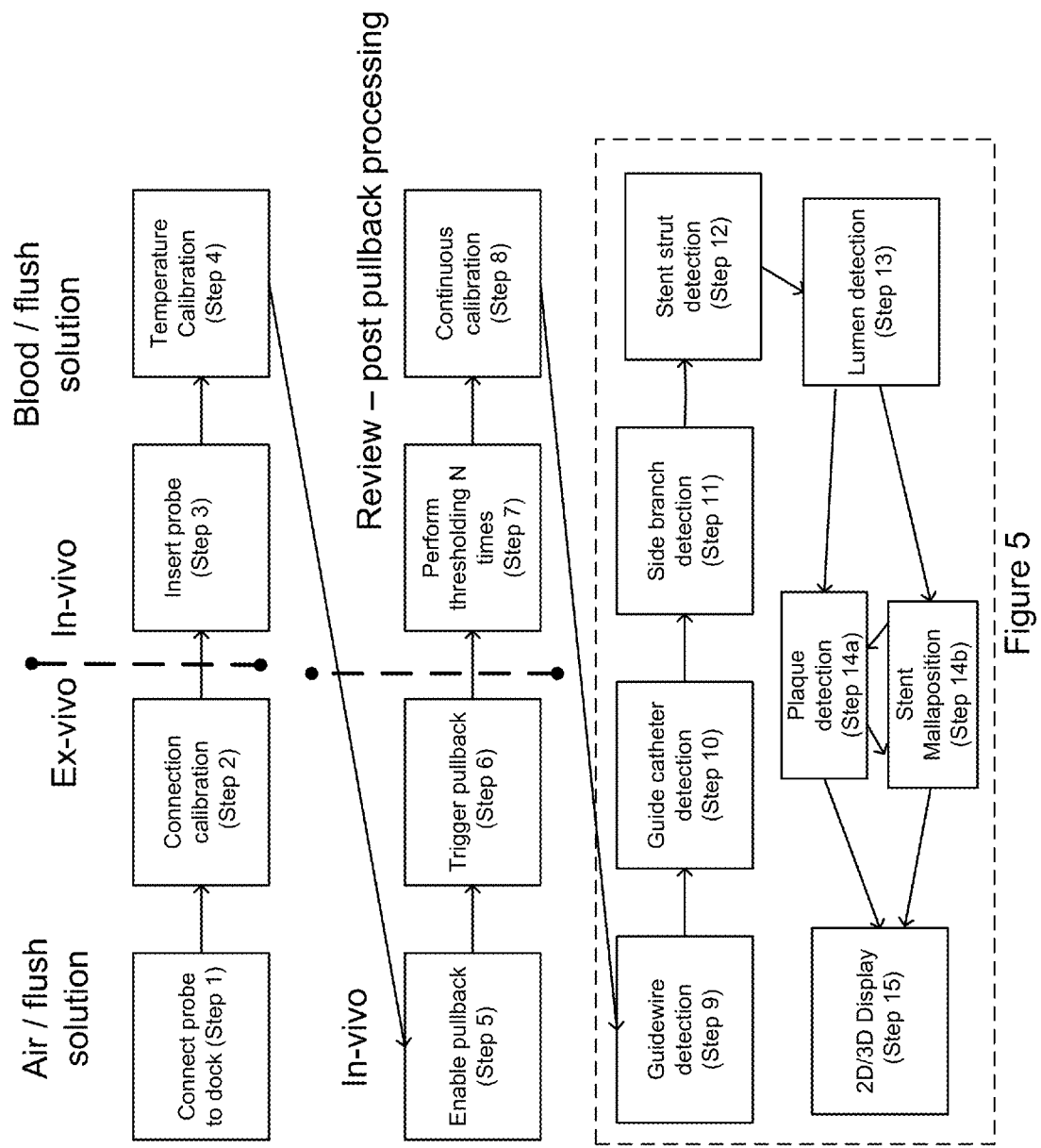

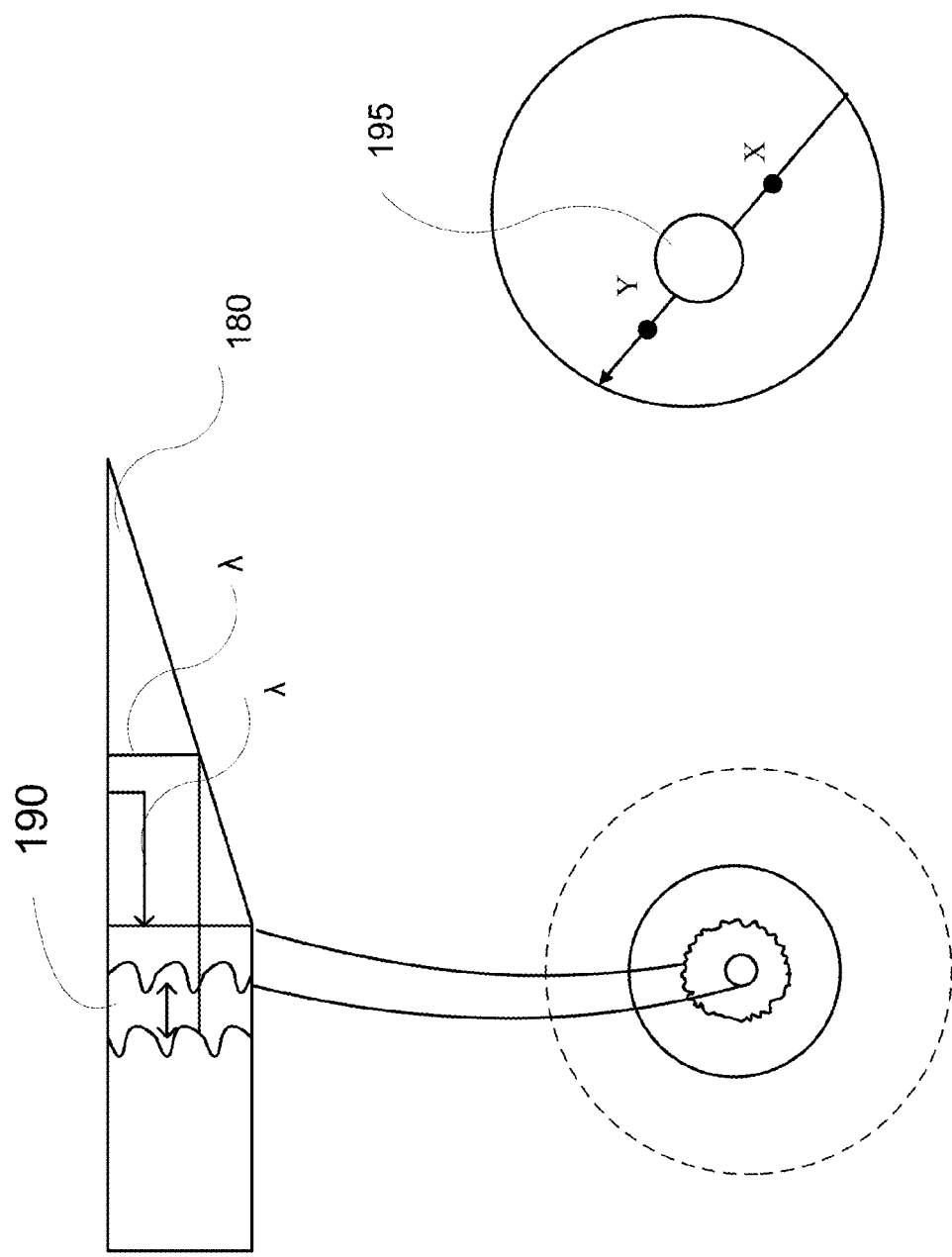

CALIBRATION AND IMAGE PROCESSING DEVICES, METHODS, AND SYSTEMS

FIELD OF INVENTION

In part, this invention relates to imaging systems, and more specifically to image data collection probes, data collection systems, optical coherence tomography and related methods.

BACKGROUND

Optical coherence tomography (OCT) is an interferometric imaging technique with widespread applications in ophthalmology, cardiology, gastroenterology and other fields. In interferometric imaging, light from a known and controlled optical path (the 'reference path') is caused to interfere with light returned from an unknown path such that information about this unknown path (the 'sample path') may be determined by an analysis of the resulting interferogram. The interferogram contains the depth location information of structures within the sample being analyzed. A particular advantage of OCT is its inherent compatibility with fiber optics making it a nearly ideal imaging modality for non-invasive or minimally invasive medical procedures.

In general, for OCT systems, the lengths of the sample and reference paths are matched to ensure the interference effect being recorded corresponds to a desired scan region within the sample. In the case of relatively long optical catheters required in many procedures (approximately 1.5 to 2 meters is common) such matching can be difficult to achieve. Furthermore, the optical fibers used in these catheters can easily stretch or contract several millimeters during use.

When using OCT, the optical 'zero-point' is critical. This defines where, in the image space, the so-called reference plane exists. By convention, surface planes are in the x-y plane, and the depth occurs along the z-axis. In a microscope application for example, it may be beneficial to set the zero point at the surface of the microscope slide, so specimens can be measured against this known surface. For a catheter inserted in a lumen such as a blood vessel, the most useful reference plane is the outer surface of the catheter tip itself, and all distances are measured outward from this location.

OCT systems typically use an adjustable reference path within the optical imaging equipment to adjust to each catheter as it is used. This is generally handled using a reference motor which can move a reflector such as a reference mirror back and forth to adjust the reference path.

A given medical application may use many disposable catheters per day; all interfaced to the same imaging equipment. Thus, while the primary path length adjustment can work quite effectively, it usually requires an initial adjustment by a skilled operator who understands the optical reflection pattern or 'signature' of the catheters that will be recorded by OCT to determine how to adjust the reference path to coincide with the outer surface of the catheter tip.

Again, the adjustment of the image zero-point, or reference plane location is performed by adjusting the primary path-length of the reference arm. This adjustment is often termed 'z-offset' of the reference arm and is controlled via a motor, called simply the z-offset motor, and a movable reference mirror. By convention, the instrument z-offset is zero when the sample arm length (catheter) is manufactured exactly as designed; is negative when the catheter is too short; and positive when the catheter is too long. Motor movements can be used to adjust the reference path in a consistent manner for different catheters.

OCT catheter-based probes typically include a beam directing structure such as lens or reflector placed at their distal tip to focus and direct light for scanning purposes. The light typically propagates through one or more transparent sheaths that comprise the catheter outer structure with an optical fiber disposed therein and in optical communication with the lens or reflector. Each of the optical interfaces can cause a reflection that will be detected by OCT. Hence, it may be challenging to determine which of those reflections corresponds to the desired optical reference point ('zero-point') of the system.

Since measurements are made based on this zero-point setting, setting it correctly can significantly affect the results of a given medical application. Furthermore, because there may be several closely spaced and similar intensity reflections, the use of software to detect the proper zero-offset ('z-offset') is problematic and unreliable. Additionally, as a further complexity, because imaging systems and the disposable catheter-based based probes such systems use change over time, software for one system is generally not designed for different OCT probes. Calibration drift and other imaging artifacts can also affect image quality during a review of frames post-pullback.

Therefore, methods, devices and systems suitable for calibrating an OCT system are needed. Given the complexity of optical interface signals, additional techniques, software modules, and devices to address such signals in the context of calibrating a data collection probe or the underlying data are needed. In addition, image processing techniques suitable for dealing with calibration drift and related issues after a pullback is complete are also needed. Further, the methods, devices, and systems should be able to work with different types of disposable data collection probes. The present invention addresses these needs and others.

SUMMARY

In part, the invention relates to various image data collection probe designs that include a calibration feature to distinguish probe types and calibrate a data collection system when using a given type of data collection probe. Methods and systems that are configured to perform continuous calibration using image processing techniques after a pullback is complete that do not rely on motor related offset changes are also embodiments of the invention. The placement or properties of a given calibration feature can be used to identify different types of data collection probes. In turn, the specific calibration steps that can be performed for a given catheter type can be specified upon identifying the type of catheter being used with an OCT system.

The invention also includes various image data processing software modules and a modular or encapsulated for such modules as well as processing methods relating to their sequential arrangement. OCT data frames can be prefetched from a database or other data store or memory for use by a first software module, such as a continuous calibration module, and subsequently prefetched for a second software module, such as side branch detection. This prefetching is extendable to a plurality of software modules such as imaging processing and filtering modules.

The use of intravascular imaging probe structural components and their optical properties such as associated intensity patterns in a frame of OCT image data can be used to identify calibration features of interest or instances where features are misidentified as a calibration feature of interest.

For example, a dark or low intensity region in an OCT image that maps to a particular structural component and its optical signature regions can be used as part of a filtering or pattern recognition algorithm to screen out erroneous optical interface signals when searching for a calibration feature of interest. In this way, splices having reflections, glass components that are substantially transmissive, and light scattering calibration features can be identified with greater accuracy. In one embodiment, calibration features which move relative to the data collection probe during a pullback are searched to perform continuous calibration after the pullback is complete using imaging processing methods and software modules.

The invention provides, in part, methods of detecting a calibration feature disposed in a vessel having a vessel wall, the vessel scanned using an intravascular imaging probe. The method includes the steps of: storing image data obtained during a pullback through the vessel in a memory device, the image data comprising a plurality of frames, each frame comprising scan lines; averaging scan lines for a first frame of the plurality of frames to obtain a speckle reduced first frame; identifying a region in the speckle reduced first frame in which the calibration feature is estimated to appear; identifying candidate samples of the calibration feature; identifying a region defined by the candidate samples using a thickness of at least a portion of the calibration feature; and fitting a curve to the candidate samples to define a boundary of the calibration feature in the speckle reduced first frame.

The invention also provides methods of detecting a calibration feature disposed in a vessel having a vessel wall, the vessel scanned using an intravascular imaging probe. The method includes the steps of: storing image data obtained during a pullback through the vessel in a memory device, the image data comprising a plurality of frames, each frame comprising a plurality of scan lines; averaging the plurality of scan lines for a first frame of the plurality of frames to obtain a speckle reduced first frame; identifying a region in the speckle reduced first frame in which the calibration feature is expected to appear; identifying candidate pixels of the calibration feature using a first spatial filter; identifying a region defined by the candidate pixels using a second spatial filter having a thickness of at least a portion of the calibration feature; and fitting a curve to the candidate pixels to define a boundary of the calibration feature in the speckle reduced first frame.

In some embodiments, the intravascular imaging probe comprises an optical fiber and a beam director in optical communication with the optical fiber. The calibration feature can be a substantially elliptical cross-section of a substantially transparent curved cover comprising a polymer. The elliptical cross section can have a first annular region and a second annular region, and the second annular region can be doped with a light scattering material. The thickness can be an annular thickness of the second annular region and wherein the second annular region is disposed concentrically within the first annular region.

In some embodiments, the method can include the step of receiving the thickness from a device attached to the intravascular imaging probe.

In some embodiments, the method can include the step of searching for the second annular region using the thickness.

In some embodiments, the method can include the steps of rotating the optical fiber and the beam director within the calibration feature and generating an image of a cross-section of the blood vessel. The image can include a first annular region having a first optical intensity and a second annular region having a second optical intensity, and the second optical intensity brighter than the first optical intensity.

In some embodiments, the method can include the steps of: averaging scan lines for a second frame of the plurality of frames to obtain a speckle reduced second frame; identifying a region in the speckle reduced second frame in which the calibration feature is estimated to appear; identifying candidate samples of the calibration feature using a first spatial filter; identifying a region defined by the candidate samples using a second spatial filter having a thickness of at least a portion of the calibration feature; and fitting a curve to the candidate samples to define a boundary of the calibration feature in the speckle reduced second frame.

In some embodiments, the method can include the steps of: averaging the plurality of scan lines for a second frame of the plurality of frames to obtain a speckle reduced second frame; identifying a region in the speckle reduced second frame in which the calibration feature is expected to appear; identifying candidate pixels of the calibration feature using a first spatial filter; identifying a region defined by the candidate pixels using a second spatial filter having a thickness of at least a portion of the calibration feature; and fitting a curve to the candidate pixels to define a boundary of the calibration feature in the speckle reduced second frame.

In some embodiments, the method can include the steps of: identifying a dark region having a first intensity in one or more of the scan lines of a frame; and excluding optical signals having a second intensity appearing in the dark region if the second intensity is greater than the first intensity.

In some embodiments, the method can include the steps of: identifying a dark region having a first intensity in a plurality of the frames; and excluding optical signals having a second intensity appearing in the dark region if the second intensity is greater than the first intensity.

In some embodiments, one or more of the identifying steps are performed using one or more filters.

In some embodiments, the method can include the step of rejecting image data associated with the boundary of the calibration feature, when a shape of the boundary is irregular or exceeds a shape threshold.

The invention also provides, in part, intravascular image data processing systems. The system can include a memory and a processor in communication with the memory. The memory includes instructions executable by the processor to cause the processor to: continuously calibrate a plurality of frames comprising cross-sectional images using an elliptical calibration feature that changes between two or more frames of the plurality of frames, the plurality of frames comprising data collected during a pullback of a probe through a blood vessel; detect a guidewire in the plurality of frames; and display a plurality of continuously calibrated frames.

In some embodiments, the continuously calibrating includes identifying the elliptical calibration feature in at least a majority of the plurality of the frames.

In some embodiments, identifying the elliptical calibration feature is performed using one or more constraints selected from the group consisting of non-concentric positioning of calibration feature, a circular profile of calibration feature, a perimeter measure of calibration feature, an area measure of calibration feature, a thickness of a brighter annular subset of the calibration feature, a thickness of a brighter annular subset of the calibration feature and thickness of a doped region of the calibration feature.

In some embodiments, the system can include instructions executable by the processor to cause the processor to divide the plurality of frames into a plurality of windows and fit a curve relative to a measurement of the elliptical calibration feature across the plurality of windows.

In some embodiments, the system can include instructions executable by the processor to cause the processor to detect one or more side branches in the continuously calibrated frames and display a side branch on one or more of the continuously calibrated frames.

In some embodiments, the system can include instructions executable by the processor to cause the processor to detect a lumen of a blood vessel on a per frame basis for the continuously calibrated frames and to display the lumen of the blood vessel in the continuously calibrated frames.

In some embodiments, the system can include instructions executable by the processor to cause the processor to detect a guide catheter on a per frame basis for the continuously calibrated frames.

In some embodiments, the system can include instructions executable by the processor to cause the processor to detect a stent strut and to display a stent strut on one or more of the continuously calibrated frames.

In some embodiments, the system can include instructions executable by the processor to cause the processor to: detect one or more side branches on a per frame basis in the continuously calibrated frames; detect one or more stent struts in the continuously calibrated frames on a per frame basis; detect a lumen of a blood vessel on a per frame basis for the continuously calibrated; and display a side branch, one or more stents struts, and the lumen on one or more of the continuously calibrated frames.

In some embodiments, the elliptical calibration feature includes a first border, and the border changes between the two or more frames.

In some embodiments, the elliptical calibration feature includes a second border disposed within the first border, and the second border changes between the two or more frames.

In some embodiments, continuously calibrating a plurality of frames includes calibrating each scan line prior to generating a frame of calibrated scan lines.

In some embodiments, the system can include instructions executable by the processor to cause the processor to: generate an alert in response to a shape of the first border or a loss of calibration feature tracking In one embodiment, one or more filter kernels are configured to identify one or more intensity patterns or data collection probe features including without limitation: a calibration feature such as an intensity pattern from an annular doped region of a sheath, a region of low intensity such as a dark ring or band associated with a glass or other substantially non-reflective structure a reflection from a splice between a first section of an optical fiber and a second section of an optical fiber, a reflection from a potting layer, and a calibration feature disposed in the imaging field which is imaged at different locations as a probe rotates.

In one embodiment, a filter kernel can be applied on a per scan line basis. In one embodiment, a filter kernel can be configured to match a high or a low region of a ring along a given scan line. In one embodiment, the first section and the second section are sections of a sample arm of an interferometer. In one embodiment, the selection of a particular filter kernel is triggered based upon a thickness of a doped annular calibration feature. In one embodiment, a thickness of a doped annular calibration feature, a scattering particle concentration of a doped annular calibration feature, or other probe-specific calibration features can be encoded using a tag which can be read by a scanner and transmitted to a calibration software module for selecting a particular filter kernel in response to the encoded thickness. In one embodiment, the tag is a near field tag or an RFID tag. The scanner can be part of a probe interface unit in one embodiment.

In one embodiment, a filter kernel such as a convolution matrix is implemented as a matrix including rows and columns and elements configured to perform image processing for performing intensifying, sharpening, pattern identification, detection, tracking and other image processing tasks. The filter kernel can be used in various preprocessing and other processing stages to perform image processing on OCT image data or other image data. In one embodiment, the term "prefetch" means to obtain data from one source in advance of such data being requested or processed by another system or process. Notwithstanding the foregoing, the scope of the terms discussed herein is not intended to be limiting, but rather to clarify their usage and incorporate the broadest meaning of the terms as known to those of ordinary skill in the art.

In one embodiment, calibration of frames of image data can be performed after a pullback is complete using image processing techniques rather than using motor position to affect a calibration. In one embodiment, different optical fiber changes following a motor-based calibration can be handled in software and performed on a per frame basis. For example, error associated with optical fiber stretching or blood vessel movement, such as due to a heart muscle contraction, can be corrected for on a per frame basis using a continuous calibration processes such as an image processing module. Tracking of moving or otherwise deforming calibration features on a per frame basis and accounting for false signals that can mimic calibration features are embodiments of the invention.

In one embodiment, an elongate sheath having a substantially circular or elliptical cross-section is doped with a plurality of scattering elements in a pattern such as a ring, a band, or other annular region or multiple annular regions. An optical probe can be pulled back with respect to the doped sheath such that image frames of data are generated in which the appearance of the pattern of the doped region changes, moves, or deforms in one or more frames along the pullback.

In one embodiment, the elongate sheath is configured to transmit light suitable for generating an image of a blood vessel or a component thereof. In one embodiment, substantially circular or elliptical cross-section includes a first substantially annular region that includes scattering elements and a second substantially annular region that is substantially free of scattering particles. In one embodiment, a calibration feature includes a ring that defines a first annular subset and a second annular subset. In one embodiment, the scattering particles are $TiO_2$ particles.

A calibration feature can include one or more filters use to track a one-dimensional or a two-dimensional feature that appears across a plurality of frames of image data. Optical signatures of catheters can be identified based on the back scattering signals received from calibration features or other sheaths used in a probe.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIGS. 2A-2D are schematic diagrams depicting cross-sections of a catheter-based intravascular data collection probe according to an illustrative embodiment of the invention.

FIG. 5 is a schematic diagram that includes the steps and stages of FIG. 4 and also depicting additional details relating to steps and stages relating for collecting image data with respect to a blood vessel and post pullback data processing according to an illustrative embodiment of the invention.

FIG. 9A is a schematic diagram depicting an intravascular image data collection probe having a beam director and one or more optical fiber splices and pattern recognition features relating thereto according to an illustrative embodiment of the invention.

FIG. 9B is a schematic diagram illustrating manufacturing variability's impact on a calibration feature which can be addressed according to an embodiment of the invention.

DETAILED DESCRIPTION

In part, the invention relates to various methods of collecting and processing data such as frames of OCT data. In one embodiment, a frame of OCT data or image data includes a cross-sectional image generated from a plurality of scan lines obtained using a rotatable intravascular probe. The cross-sectional images or other images are generated using interference-based depth measurements obtained with respect to a sample such as a blood vessel using a data collection probe. One embodiment of the invention relates to methods of calibrating a data collection system such as an OCT system used in conjunction with a data collection probe. Various types of calibration can be used such as manual calibration or user triggered automatic calibration using a mirror and motor initiated changes. In part, the invention relates to continuous calibration method embodiments that calibrate frames of OCT data from a pullback in conjunction with an image processing module rather than motor adjustments.

Data collection probes, such as OCT probes, IVUS probes, pressure wire-based probes, fractional flow reserve probes, probe combining the foregoing technologies, are inserted into a subject and then used to image a particular blood vessel or otherwise collect data with respect to such a vessel. As a result, the data collection probes are disposable in nature. The feature set and method for calibrating such probes can change over time. Some of these probes may be backwards compatible and forwards compatible with existing imaging systems and systems that will be developed in the future. In contrast, some of the probes may only be compatible with certain types of OCT systems or only certain features of a given probe can be used with a given system. Accordingly, being able to identify different types of probes and how they work with a given OCT system is a desirable design feature. In addition, the calibration routine used with a given current generation probe and a legacy probe type may be different. As a result, detecting such differences allows different calibration routines to be used.

In addition, the data collection systems that interface with and receive data from such probes also change over time. As a result, one aspect of the invention relates to recognizing and calibrating different types of data collection probes. In part, in one embodiment, different calibration routines are selected from a plurality of software modules or data processing stages based upon the type of data collection probe that is coupled to a particular data collection and processing system.

Figure 1A:
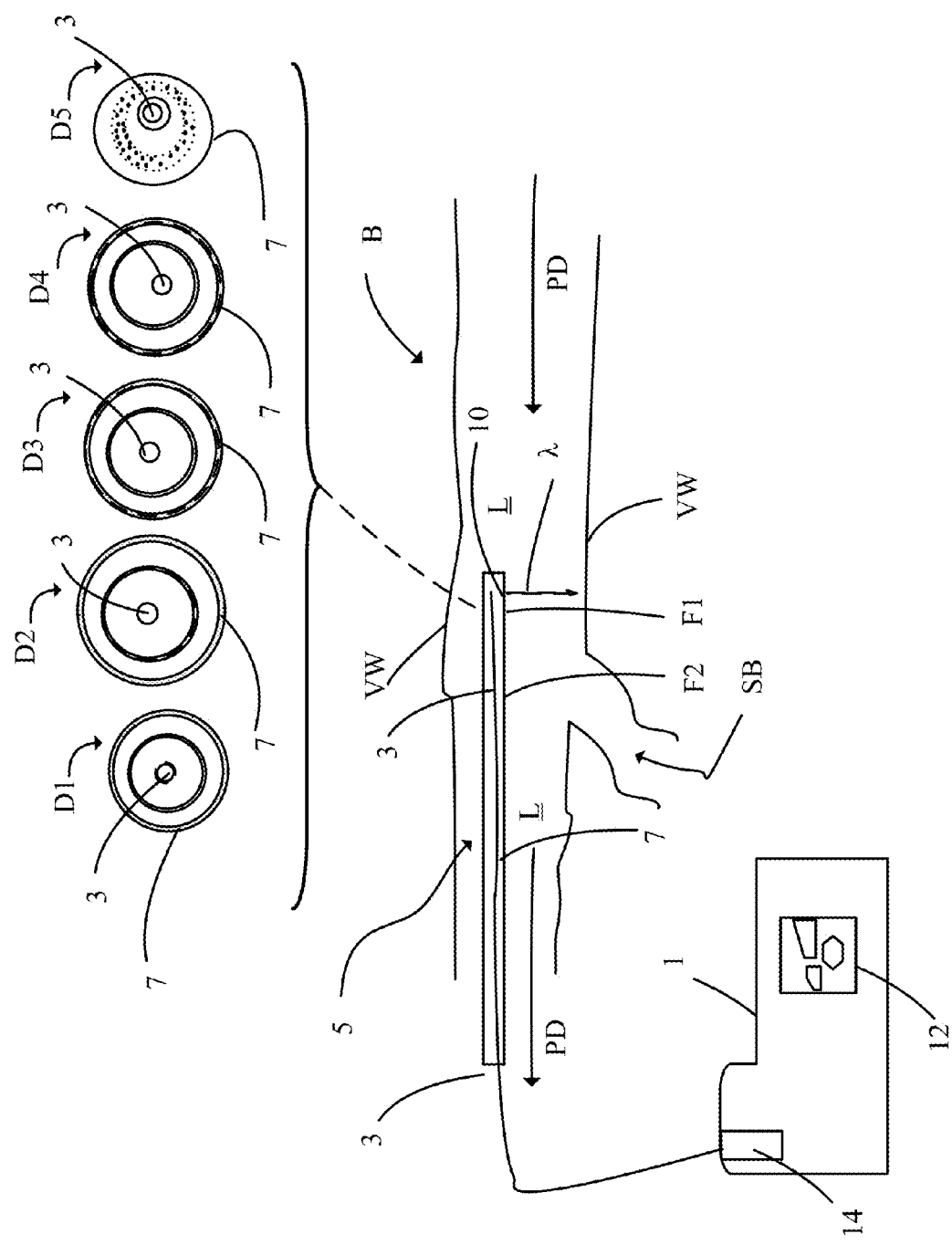
FIG. 1A is a schematic diagram depicting various data collection probe configurations suitable for use with an optical coherence tomography system and one or more calibration processes according to an illustrative embodiment of the invention.
Figure 1B:
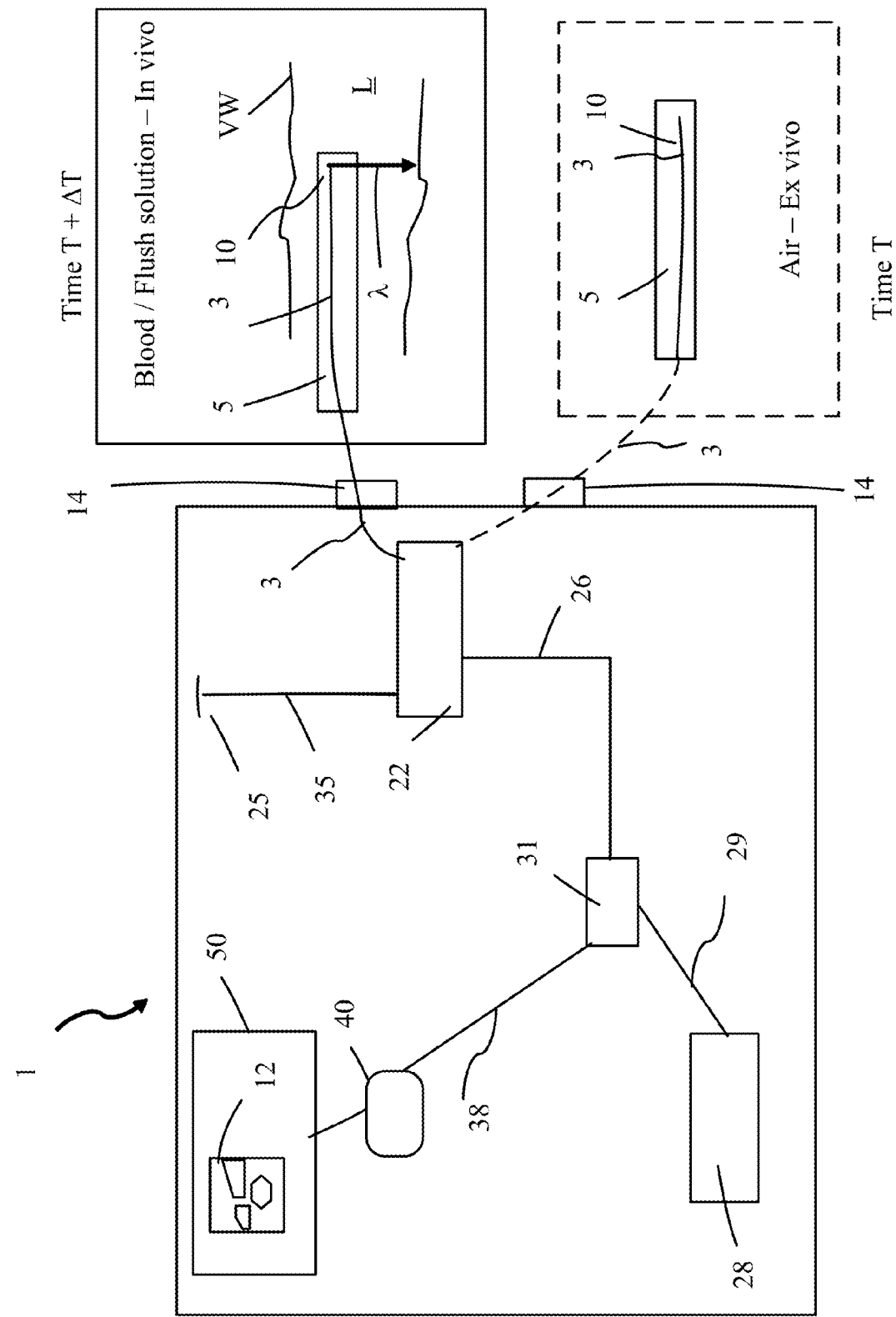
FIG. 1B is a schematic diagram depicting an OCT data collection system and an intravascular data collection probe according to an illustrative embodiment of the invention.

In FIG. 1A an image data collection and processing system 1 is shown that is configured to interface with an optical fiber 3 that is part of a data collection probe 5. FIG. 1B shows additional details relating to the image data collection and processing system 1 for an embodiment in which it is an OCT data collection and processing system. The probe 5 is shown in an in-vivo environment with respect to a blood vessel B having a vessel wall VW that defines a lumen L. The blood vessel B also includes a side branch SB.

The probe 5 includes a probe tip which includes or is in optical communication with an optical fiber 3. The optical fiber 3 and the tip of the probe 5 are disposed within one or more sheaths such as catheter sheath 7. The probe tip can include various elements such as an angled beam director or a lens cap as well as transducers for other imaging modalities. The optical fiber 3 of the probe 5 can also include a torque wire disposed around the fiber 3. The probe transmits light, shown as λ, in the lumen L and receives light scattered from the vessel wall VW.

In one embodiment, the optical fiber 3 is a portion of a sample arm of an interferometer. A data collection probe 5, such as an OCT probe, can be used to collect depth information suitable for imaging a sample such as a blood vessel. For example, a set of frames of image data, such as frame F1 and frame F2, are generated based upon optical signals sent and received by such a probe 5. A cross-sectional image of blood vessel is formed by a collection of scan lines as the probe rotates.

The probe 5 is pulled back through the blood vessel B as the fiber 3 and probe tip within sheath 7 rotates such that the beam of light λ sent to the vessel wall from the probe tip traces a spiral as it moves along the section of the blood vessel B being imaged. This section has a specified pullback distance. A set of frames are obtained with regard to the pullback distance in one embodiment. The probe 5 slides within the sheath 7 as it is pulled back through the blood vessel. As a result different frames are obtained with regard to different sections of the blood vessel and through different sections of the sheath 7. For example, frame F1 and frame F2 represent in FIG. 3B and FIG. 3C correspond to imaging through the sheath 7 at different locations and showing images generated with regard to different calibration features as a result of the different sections of sheath 7 being imaged.

As a further example, the sheath 7 may move and compress along the blood vessel B and have different elliptical cross-section that varies or move along the frames as shown in frames F1 and F2. In part, one aspect of the invention relates to performing calibration of a plurality of frames of OCT data using a calibration feature 10 that changes across frames as well as calibration features that do not move across frames. A fiber fixed calibration feature 10a that is directly attached to the optical fiber 3 such as probe embodiment D1 of FIG. 2A is different from a calibration feature in the imaging field that moves and changes as the probe 5 is pulled back such as calibration feature 10c in FIGS. 2C and 2D. In FIG. 2A, the probe D1 includes a calibration feature that is attached to the optical fiber 3 as a concentric layer and thus moves with and is consistently imaged the same way by the probe D1.

Different types of data collection probes can be used with a data collection system 1 and the system is configured to recognize the different types of probes such as probe 5 and other designs. Embodiments of the invention are also directed to the data collection probes and components thereof. An image data collection probe 5 such as an OCT probe can include a calibration feature 10 that can be identified by one or more modules 12 of system 1 in frames of image data obtained during a pullback. The software modules 12 can include various calibration software modules, image processing software modules, graphic user interface, cross-sectional area display, longitudinal or L-mode display, a spline or interpolation software module, prefetch software module or architecture, and other software modules as described herein.

In one embodiment, the calibration feature 10 includes a geometric structure or pattern or controlled arrangement of backscattering particles to distinguish probe types and calibrate a data collection system when using a given type of data collection probe. The placement or properties of a given calibration feature can be used to identify different types of data collection probes. In turn, the specific calibration steps, such as steps 1-4 shown in FIG. 4 that can be performed for a given catheter type can be specified upon identifying the type of catheter being used with an OCT system. For example, with regard to FIGS. 2A-2C, the different calibration features 10a, 10b, 10c, and combinations thereof can be used as signatures to differentiate probe types and trigger probe specific calibration software routines. Different calibration modules can be stored in memory as part of software modules 12 used by the system 1.

In one embodiment, the optical fiber 3 interfaces with a patient interface unit 14 that includes a dock or coupler configured to receive an end face of optical fiber 3 or an optical fiber coupled to optical fiber 3. The PIU can include a tag reader such as an RFID reader to read tags attached to the probe 5. Information relating to calibration features such as the thickness or concentration of doped sheaths or layers of the probe can be encoded thereon.

The top portion of FIG. 1A show various possible exemplary cross-sections D1, D2, D3, D4, and D5 of a given probe 5. As shown, a data collection probe 5 can include a plurality of elongate nested layers or sheaths and an optical fiber 3 disposed therein. The data collection probe can include a calibration feature such as the calibration feature 10 and other specific examples of calibration features such as features 10a, 10b, 10c and others shown and discussed in more detail herein.

The data collection probe 5 can include a plurality of surfaces that provide reflections that can be used to identify one or more components of a given type of data collection probe. The layers shown are typically elongate cylindrical objects such as sheaths that are disposed one inside of the other. In one embodiment, a support material such as a potting material surrounds an optical fiber 3 disposed along the longitudinal axis of the probe in various embodiments. An example of a fiber 3 having potting material 20 surrounding the fiber 3 and one or more sheaths is shown in FIG. 1A with regard to cross-section option D1 of the probe 5.

The data collection probe 5 is an OCT probe in one embodiment. The probe 5 is generalized as shown because various different exemplary cross-sections for OCT probe configurations are possible. As such, probe configurations having cross-sections such as the optional probe cross-sections D1, D2, D3, D4, D5, D6 are provided as examples of various sheath configurations and the associated variations in calibration techniques associated therewith. Additional details relating to the various probe configurations D1, D2, D3, D4, and D5 are discussed with regard to FIGS. 2A-2D and FIGS. 3A-3D.

In part, the invention relates to devices, probes, systems, components thereof and methods suitable for collecting data with respect to a sample such as a blood vessel such that a suitable image can be generated with respect to the sample. In order for a suitable image to be generated, components of the data collection system need to be identified and calibrated. In particular, identifying different types of data collection probes is of interest because as imaging systems such as OCT systems change over time and as probe designs changes, it is desirable know if the relevant features of a given imaging system can be used as well as if certain legacy probes are compatible with a given imaging system. Prior to discussing such features and cross-sectional configurations, in FIGS. 2A-2D and FIG. 3A, it is useful to consider some additional details relating to system 1 when such a system is an OCT system.

In FIG. 1B, a generalized data collection and processing system 1 is shown. A data collection probe can be connected to the system 1 via various mechanisms such as optical coupler 22. As shown on the right, the data collection probe 5 can be connected in air or ex vivo state and then inserted in a blood vessel having a lumen L. The system includes an interferometer having a reference arm and a sample arm. Optical fiber 3 is part of the sample arm of the interferometer. A reflector 25 such as a movable mirror on a track is part of the interferometer and specifies one terminus of the reference arm. The first optical coupler 22 is in optical communication with a second optical coupler 31 via optical path 26 in one embodiment.

A light source 28, such as a swept source, produces light that passes by way of an optical path 29 into the second optical coupler 31. Light entering the first coupler 22 is the split along optical fiber paths 35 and 3. One path 35 terminates at a movable reflector 25, while sample arm portion enters probe 5 and allows light to be directed to the vessel wall VW at an angle relative to the longitudinal axis of the probe. Various types of probes 5 having different components such as back scattering doped sheaths or back scattering components can be used as calibration features. The optical patterns that are generated in a given image from a given probe are also types of calibration features.

Light reflected by the movable reflector 25 passes back along optical fiber 35 to the coupler 22. Similarly light reflected by wall VW passes back along optical fiber 3 to the coupler 22 and combines with the light reflected by the movable reflector 25 to form an interference pattern. This combined light passes through optical path 26 to second coupler 31 to optical fiber 38 and is detected by a detector 40 such as a photodiode. The output signal from the detector 40 is processed by a processor or other components of an OCT system 50.

Figure 3A:
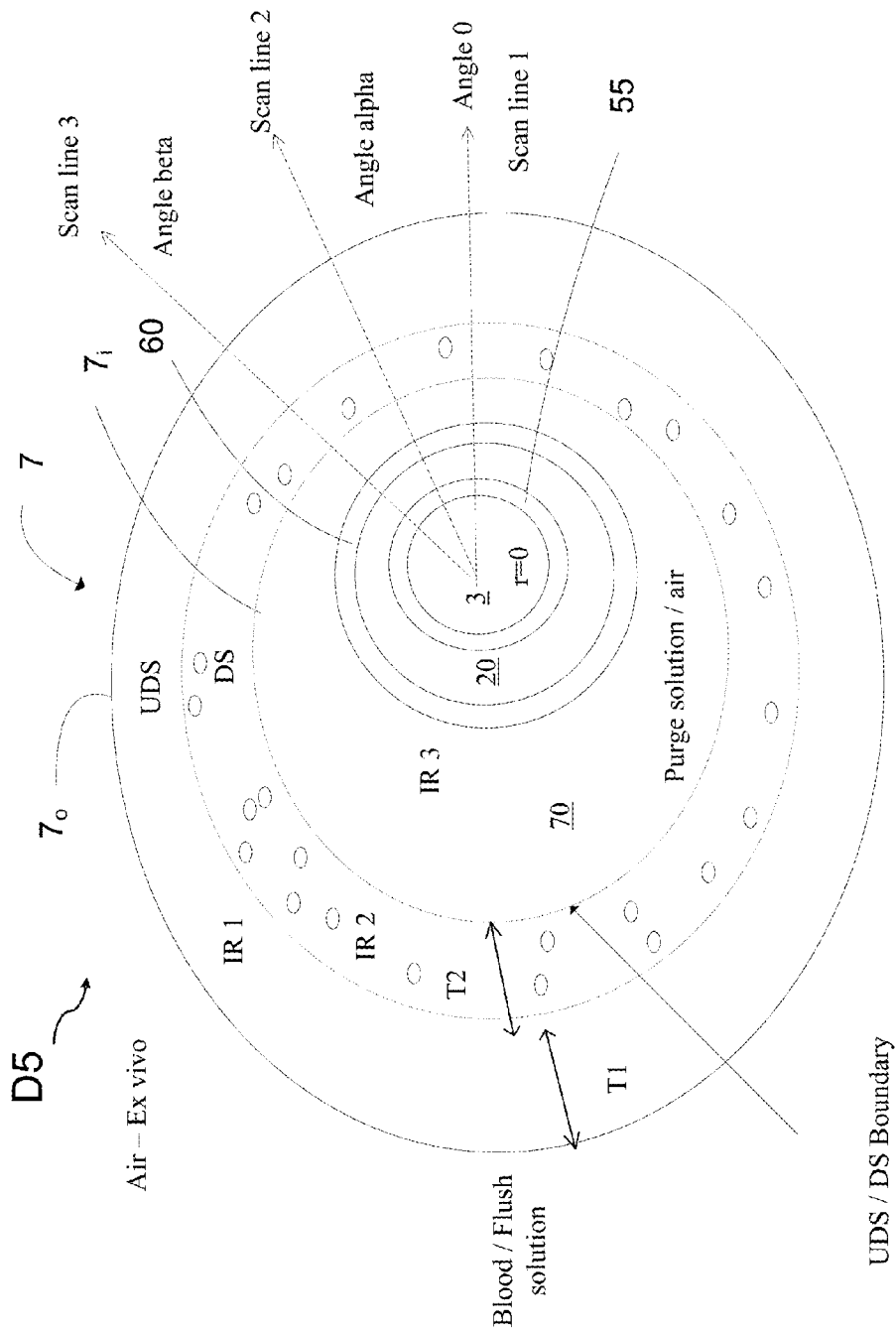
FIG. 3A is a schematic diagram depicting a cross-section of a catheter-based intravascular data collection probe along with additional details relating to scan lines and certain calibration features according to an illustrative embodiment of the invention.
Figure 3B:
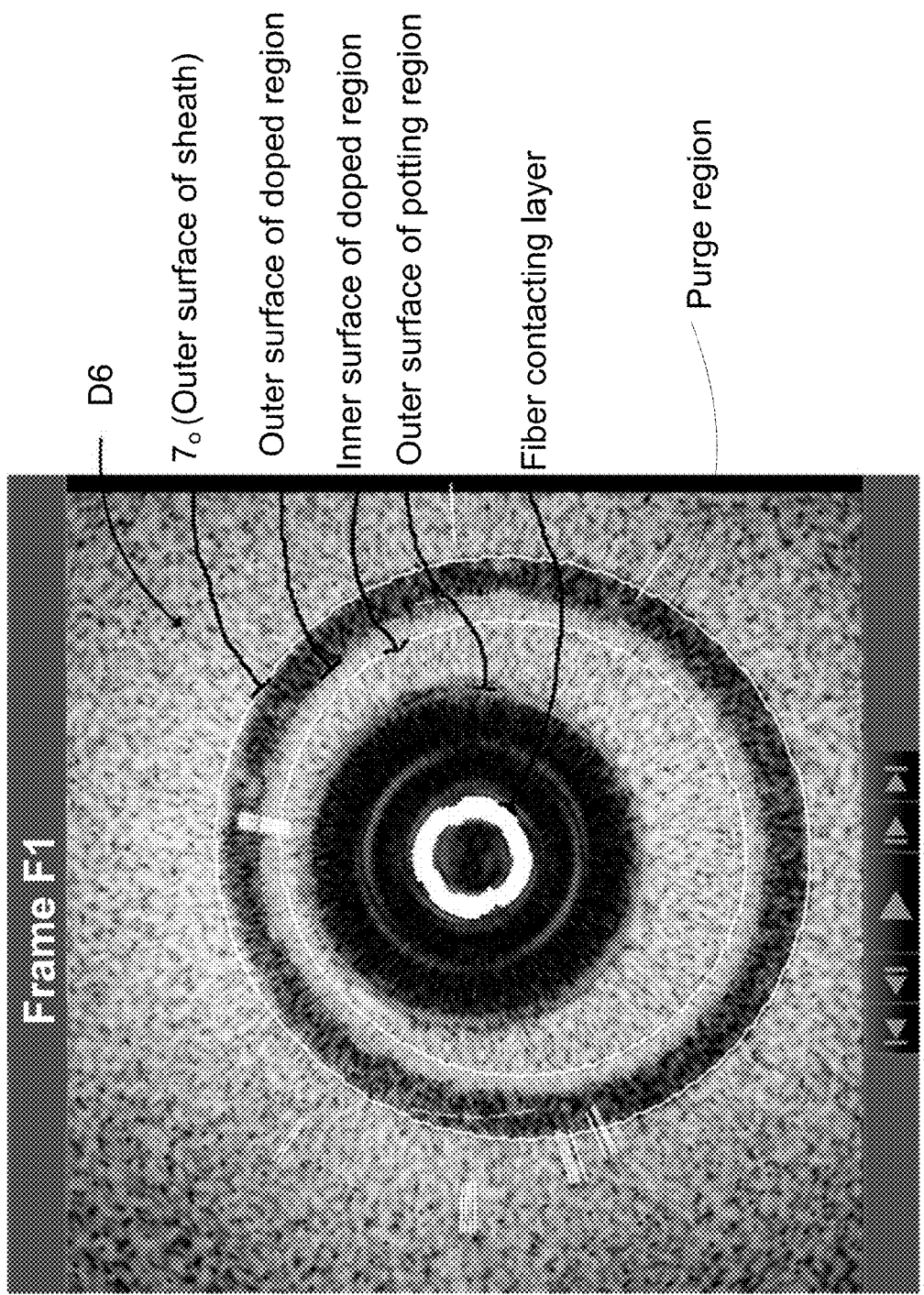
FIG. 3B is a frame of optical coherence tomography image data obtained with respect to a blood vessel at a first frame using an OCT probe that includes various optical features including one or more calibration features according to an illustrative embodiment of the invention.
Figure 3C:
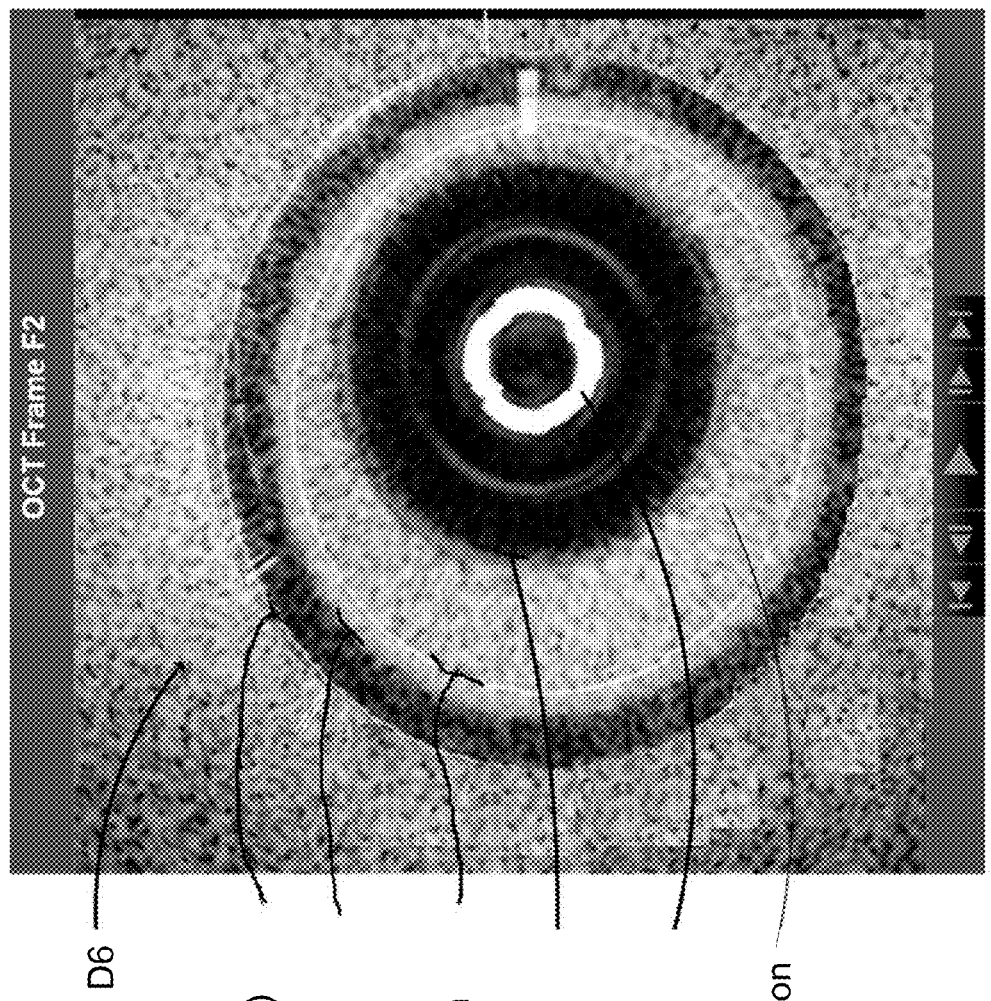
FIG. 3C is a frame of optical coherence tomography image data obtained with respect to a blood vessel at a second frame using an OCT probe that includes various optical features including one or more calibration features according to an illustrative embodiment of the invention.

In one embodiment, the OCT system 50 is a workstation or server configured to run software modules 12 and process frames or scan lines of image data corresponding to cross-sections of the blood vessel showing features of the vessel wall such as shown in FIGS. 3B and 3C for frames F1 and F2. The probe 5 includes or images one or more calibration features 10 during a pullback through a blood vessel. In one embodiment such as regions of light scattering particles that can be imaged and recognized using one or more software modules 12 and used to calibrate frames of image data.

Since OCT has difficulty resolving a blood field relative to the vessel wall VW when a probe 5 is disposed in a lumen L, a flush solution is used to clear the blood field and promote a good imaging environment. Contrast solution can flow through an annular region, a purge lumen defined by an inner layer, such as a first layer or first sheath, and an outer layer, such as a second layer or a second sheath as shown.

In contrast, as shown at the bottom right portion of FIG. 1B, at a time T prior to insertion in a lumen, when the probe 5 is in air, this region can be air filled prior to use such as the ex vivo scenario shown in which the probe 5 is not disposed in the lumen L. The air is purged and a suitable solution such as a contrast solution or another solution fills one or more cavities or volumes in a given probe 5. At a later time, T+ΔT, when the probe is in the lumen, the outer sheath of the catheter is adjacent a blood field in a blood vessel such as an artery in contrast with the outer sheath being adjacent to air at time T. The different air and fluid interfaces can be calibration features in one embodiment.

The presence of air and a fluid in the catheter can be used during calibration because of the different optical propagation and reflections that occur based on which material is in the optical path during data collection. For example, the interface between various sheaths and fluids and air changes as shown in the cross-sections of FIGS. 2A-2D and 3A depending on whether the probe is calibrated in air prior to insertion in a lumen or calibrated when in place. A purge lumen 70 is shown in the probes of FIGS. 2A-2C.

One way in which data collection probes differ relates to the characteristics of calibration features, such as doped layers or regions used in a given probe, as well as how such calibration features are positioned and which sheaths or layers are doped. The calibration features can include a scattering material arranged in a pattern such as a layer within a component of the probe. In one embodiment, the scattering material includes $TiO_2$. Fractional doped layers can also be selectively doped in one or more annular regions doped to form bands or regions of a sheath that scatter light.

FIGS. 2A, 2B, 2C, 2D, 3A, and 3B show various cross-sections of exemplary intravascular imaging probes D1, D2, D3, D4, D5, and D6 that include an optical fiber 3 and a sheath 7 having an outer sheath layer $7_o$ and inner sheath layer $7_i$ and calibration features or other properties suitable for performing calibration. FIG. 2A depicts a cross-section of an intravascular imaging probe D1. Several substantially concentric layers surround an optical fiber 3. For example, the optical fiber 3 is surrounded by a polymer layer 55 such as PET or another suitable polymer. With respect to probe D1, polymer layer 55 is doped with light scattering particles. In one embodiment, the light scattering particles in and of themselves are a calibration feature 10a. This polymer layer 55 can be doped and shrunk onto the catheter lens to induce back reflection and generate a bright ring in a given image frame. Given the attachment to the lens, this calibration feature does not move across frames of image data.

In another embodiment, the light scattering particles together with the polymer layer 55 are a calibration feature 10a. In one embodiment, a potting layer 20 surrounds polymer layer 55 and optical fiber 3. The potting layer 20 can also be surrounded by another polymer layer 60. In one embodiment, this additional polymer layer 60 can also include PET or another suitable material. This polymer layer 60 can be doped as a calibration feature as shown in FIG. 2B. As shown, the outer sheath $7_o$, which is also typically formed from a suitable polymer, is the outer surface of the probe which typically interfaces with either air, prior to purging and insertion, or a flush solution during purging, or a flush solution such as contrast agent when disposed in a blood vessel. Purging the probe occur in the purge lumen 70. Each of the layers or structures shown in FIGS. 2A-2D are elongate sheath or optical cores.

FIG. 2B depicts a cross-section of an intravascular imaging probe D2 in which polymer layer 60 is doped to form calibration feature 10b. Other layers of a probe 5 such as layers 55 and sheath 7 can also be doped such as between inner sheath layer $7_i$ and outer sheath layer $7_o$ as shown by the calibration features 10c in probes D3 and D4. In probe D4 of FIG. 2C, the optical fiber 3 is misaligned relative to center position C. In contrast, in FIG. 2D, optical fiber 3 is substantially in the center of potting layer 20.

Figure 3D:
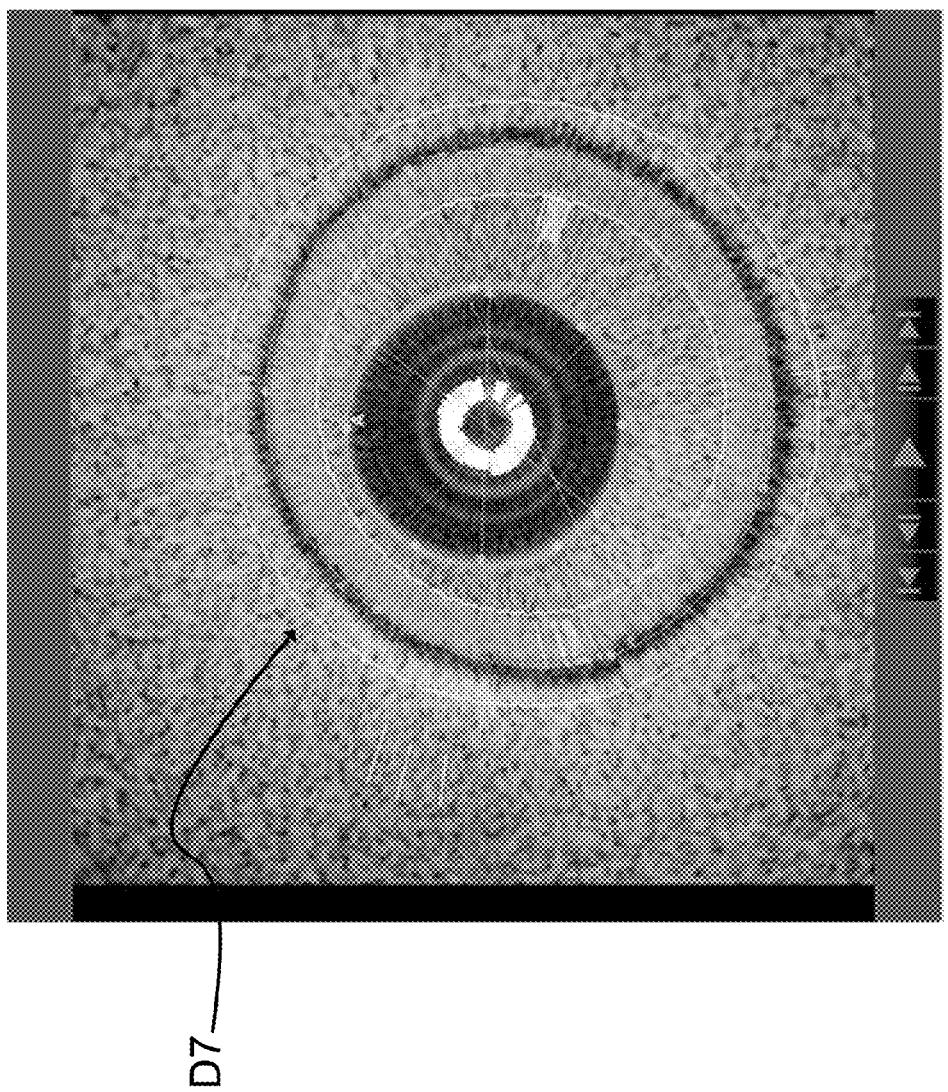
FIG. 3D is a frame of optical coherence tomography image data obtained with respect to a blood vessel including one or more calibration features according to an illustrative embodiment of the invention.

Additional details relating to exemplary cross-section of intravascular data collection probe D5 and D6 are shown in FIGS. 3B, 3C, and 3D. With respect to data collection probe D5 of FIG. 3A, the probe includes a calibration feature disposed in sheath 7. Specifically, a region of the sheath is undoped UDS and has a thickness T1 and an index of refraction IR1. The sheath 7 is partially doped such that the doped portion of the sheath DS having a thickness T2 and an index of refraction IR2 is adjacent a flush zone 70 having an index of refraction IR3. The doped region of the sheath DS includes a concentration of scattering particles sufficient to scatter light for collection by a beam director or lens (not shown) and fiber 3.

FIGS. 3B and 3C show additional details relating to various layers of an exemplary data collection probe D6. FIG. 3D show additional details relating to various layers of an exemplary data collection probe D7. FIGS. 3B and 3C show examples of an elliptical calibration feature that includes a second border disposed within a first border. In one embodiment, the borders can include circles or rings in the image or borders or other calibration features.

An OCT image, such as the cross-sectional images of FIGS. 3B, 3C, and 3D are typically acquired one scan line at a time. A sequence of samples along a ray originating at the catheter center to the maximum imaging depth is referred to as a scan line in one embodiment. In one embodiment of the invention, the smallest data unit in an OCT image is called a sample. A sequence of samples along a ray originating at the probe center to the maximum imaging depth is called a scan line. An OCT image is typically acquired one scan line at a time. A cross-sectional image can be formed from a set of scan lines collected as the probe rotates. Further, to image a segment of an artery or other vessel, the catheter is moved longitudinally while rotating. In this way, the probe acquires a set of cross-sectional images in a spiral pattern. The images originate from the various scan lines associated with a slice of the vessel or artery of interest. As an example, scan lines 1, 2 and 3 are illustrated with respect to FIG. 3A. The scan lines are arranged with angles between them like spokes on a wheel.

A cross-sectional image can be formed from a set of scan lines collected as the probe rotates. Further, to image a segment of an artery or other vessel, the catheter is moved longitudinally while rotating. In this way, the probe acquires a set of cross-sectional images in a spiral pattern. For a given scan line, a region of scattering can be a linear segment on the line. Various filters can be configured to be matched on a per scan line basis to identify regions of interest such as doped or backscattering regions and undoped or substantially non-scattering regions. In one embodiment, the software modules described herein are configured to operate or process a sample, a combination of samples as a scan line or a portion or a subset thereof, a combination of scan lines such as frame or a portion or a subset thereof and combinations of the foregoing. For example, in one embodiment continuous calibration is performed using samples or combinations of samples as scan lines.

The resultant two and three dimensional images originate from the various scan lines associated with a slice of the vessel or artery of interest. The image can be displayed as cross-sections, such as in FIGS. 3A-3D. The combination of cross-sectional images allow a tomographic image such as the three-dimensional perspective views or two-dimensional longitudinal views to be displayed using software modules that operates on or otherwise transforms the OCT data acquired during a pullback.

Figure 4:
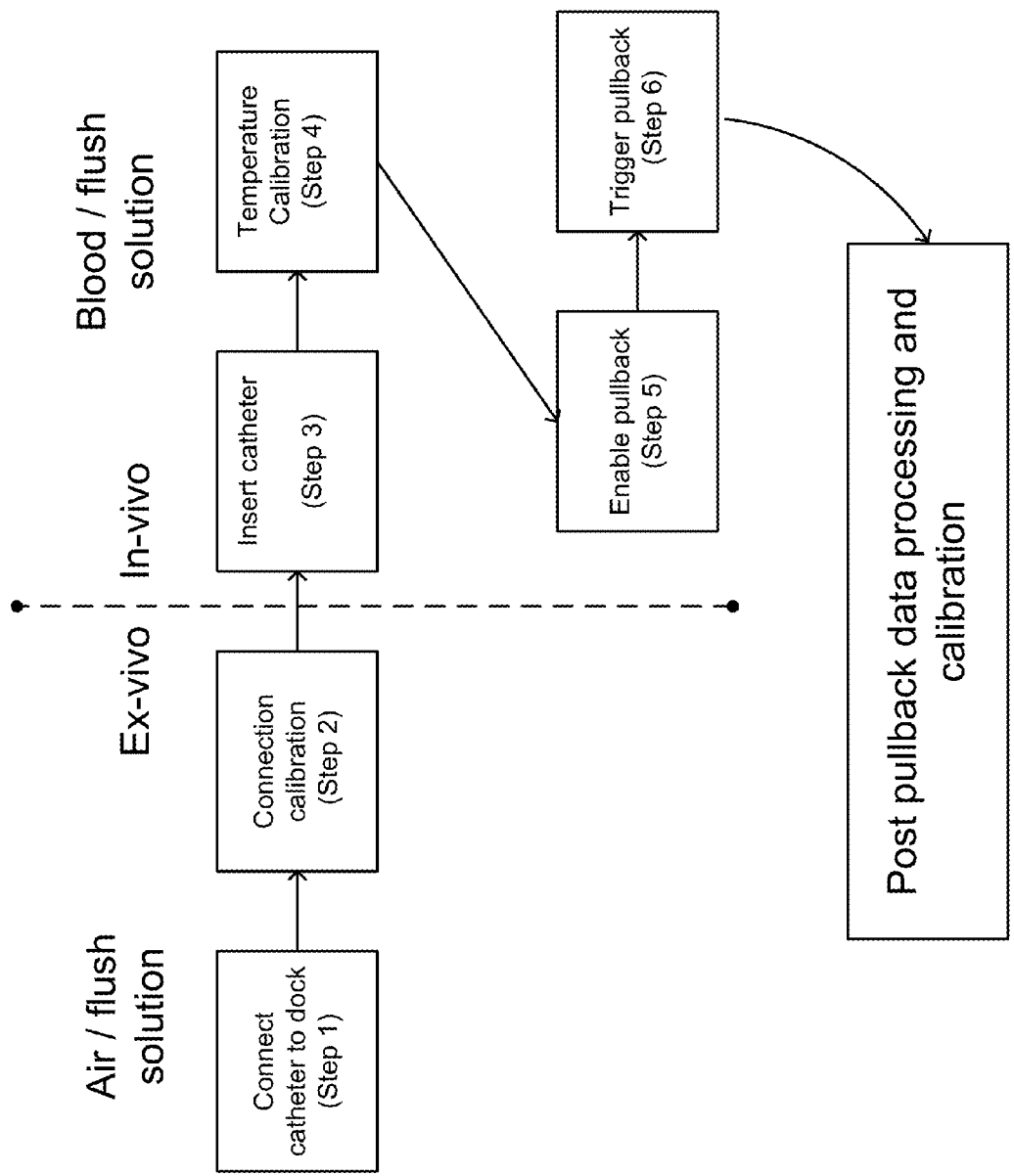
FIG. 4 is a schematic diagram depicting various high level steps and stages relating to collecting image data with respect to a blood vessel and post pullback data processing according to an illustrative embodiment of the invention.

FIGS. 4 and 5 illustrate a high level summary of events for various types of calibration. Initially, as part of the setup process for collecting OCT data, prior to performing a pullback, a disposable data collection probe is connected to a patient interface unit (step 1). Connection calibration can include a search of a range of the motor used to move the reference mirror to locate the catheter to detect scan line inversion. The frequency aliasing that occurs and can result is performed at the connection calibration and as part of the continuous calibration. The auto calibration also uses a process to compensate for image inversion or bowing as a result of frequency aliasing.

With respect to temperature related pre-pull back calibration, the sweep range of the motor is reduced such as a sweep window of a few millimeters as the length of the fiber does not change after reaching equilibrium after being inserted in a blood vessel prior to pullback.

The light propagates through one or more transparent sheaths that comprise the catheter outer structure. Each of the interfaces can cause a reflection that will be detected by OCT. Hence, it may be challenging to determine which of those reflections corresponds to the desired optical reference point.

As part of an OCT system, optical path lengths for a reference arm and sample arm of the interferometer used in the system need to be maintained within certain limits for interference to occur. This can be achieved using a translatable mirror on a track or otherwise driven in a linear manner. In this way it is possible to adjust reference arm position to align the distal tip of catheter with optical path length in the reference arm. Optical index and expansion can change optical path length in body. Various indexes of refraction (IR) are shown in FIG. 3A as well as different media (blood, flush, air, etc.). The media in which the catheter is disposed change given the time outside a patient, the flush stage, the pullback, and again at removal. The reference mirror can be moved to match the path length change as part of an auto calibration process. This is performed before pullback in one embodiment.

The calibration method is implemented as computer-based algorithm such as various steps and loops with different phases or stages. In one embodiment, the calibration method determines the type of data collection probe attached to the system bases on the presence or absence of certain features in the images generated using data collected by a given probe. In one embodiment, the method identifies a light scattering calibration feature such as a calibration feature disposed in the probe such as a doped layer.

In one embodiment, the calibration feature is disposed near the optical fiber such as by being adjacent to the optical fiber in a material contacting an out surface of the optical fiber. The calibration software module is configured to change the underlying data such that it is passed through the image data processing pipeline in a changed state. Other modules append their changes without changing the underlying data and are passed to the next image processing module with the image data and information and changes from a proceeding pipeline module.

At this point the connection calibration is performed to obtain data about the catheter from a scan of the doped sheath. The scanning for calibration can be at first rate of rotation. In general, by using a dopant which scatters light within a given data collection catheter such as near the optical fiber or set off a distance from it in the sheath, the system can determine which version of the catheter is being connected to the PIU. For example, one catheter includes a doped layer that is disposed next to the optical fiber disposed in the sheath (see FIG. 2A). In contrast, another catheter includes a doped version of the sheath (see FIG. 2D). The sheath is separated from, but substantially coaxial with, the longitudinal axis of the optical fiber.

A probe, such as probe 5 in FIG. 1A, having a rotatable optical fiber 3 is then inserted into the patient (step 3). Next there is a temperature calibration process that is performed in vivo to compensate for temperature effects on the length of the optical fiber 3 (step 4). The temperature calibration can be implemented using movement of the reference mirror such as was done with regard to connection calibration (step 2). The temperature calibration typically takes a shorter period of time relative to the connection calibration.

Next, pullback is enabled (step 5). This step can include monitoring relating to the image data from the probe and preparing a flush. A pullback is then triggered either automatically or manually (step 6). A blood clearing detection method can be used to trigger a pull back after a flush sufficiently clears the lumen.

During the pullback a plurality of frames of data is collected. OCT data received from the catheter can be saved in various formats such as a multipage TIF file format. Each TIF file includes multiple frames of data. The scan lines are acquired in a polar format in one embodiment and stored in the TIF file. Each frame is a cross-section of a blood vessel or other sample. The software-based continuous calibration method operates on the frames and aligns the catheter in each frame relative to the catheter in other frames by identifying a boundary such as a ring or doped sheath and making adjustments as to the catheter's position on a per frame basis.

One advantageous feature of the software related features described herein relate to the imaging processing pipeline. In one embodiment, continuous calibration is one image processing module plurality of image processing modules arranged in path or graph of a particular processing order. For example, the pattern can be a sequential arrangement modules that is been next that is been experimentally determined to improve quality of the OCT data for particular image frame or otherwise improve the operation downstream image processing modules.

Additionally the pattern or order of the sequence in which image processing modules are arranged can also be determined based on physiological considerations such as the interplay of a guide wire, guide wire shadows, a guide catheter, the side branches disposed in the blood vessel, stent strut detection, position of the lumen border, the detection the lumen such as by the luminal border, plaque detection or other physiological segmentation of a blood vessel, stent malaposition, in the display of two-dimensional views of a vessel such as a longitudinal view or L mode or a cross-sectional view. Additional details relating to the arrangement of image processing software modules or possible processing pathways between such modules is provided in FIG. 8.

Returning to FIG. 4, as a result of continuous calibration, frames of data obtained during the pullback have been processed such as by adjusting them to have their correct reference point consistent with path length, the sample arm and the reference arm being substantially equal or otherwise within permitted tolerances. The calibrated pullback image data is then processed by subsequent image data pipeline process processing modules shown in FIG. 4 generally and in more detail in FIGS. 5 and 8. In this way prior to performing other detection or image transforming stages all or a majority of the frames in the pullback are calibrated to improve the results of subsequent processing software modules by having the modules operate on calibrated image data instead of uncalibrated image data.

Next the images/frames are modified by first establishing a threshold for background noise or otherwise performing a thresholding process (step 7). Under the multi-frame architecture, prior frames are delivered to the thresholding algorithm to determine a threshold that will not result in too much noise in the cleared lumen or too many "drop outs" (blank areas) in the lumen boundary. The thresholding process can be implemented in one, two, three or more stages. Various thresholding algorithms can be used as is known in the art.

After thresholding, a continuous calibration process is started place to continually calibrate the diameter or position of the catheter using frames acquired as it was pulled through the lumen (step 8). The calibrate frames are then used in calibrated form for the other modules in the pipeline. Next guidewire detection is performed (step 9) and in the future, guide catheter detection will be performed (step 10). Once the artifacts of the system guidewire and noise are removed, side branch detection is performed (step 11) and stent strut detection (step 12) can be performed.

In the multi-frame architecture, image data from the pullback is stored in memory such as in a cache. The image data is then distributed to the individual modules for analysis or modification. Single frame detection and processing can be performed on the image data in one embodiment on a per module basis. In addition, the data is sent to memory storage, such as a server or hard disk, so that the individual software modules or algorithms can request and receive previous frames of OCT image data.

Once side branch detection is accomplished, the system searches for stent struts (step 12) and then determines the lumen location (step 13). Plaque detection, stent malapposition detection, or other tissue characterization can then be performed (steps 14a and 14b step 17). 2D or 3D display is then performed (step 15) using the processed OCT image data.

Continuous Calibration

Ellipse detection algorithms can be used to identify one or more sheath boundaries or interfaces between the flush solution region, blood, or one or both of the sublayers. This information can be used to align the catheter on a per frame basis. The direction of motion of the reference mirror and its speed can be used to compensate for frequency alias effects.

In one embodiment, determine which catheter is being used and to perform one or more calibration processes, the reference mirror is set at a home position. This is typically performed before a pullback as part of an autocalibrate step. Next, it is swept or scanned in the forward direction to a first position. A course adjustment scan can then be performed in the backward direction beyond where it needs to be (to remove hysteresis). A fine adjustment is then made in the direction of the original sweep. Next using the scan lines obtained for a given frame, the software-based system attempts to find a partial layer or full layer of scattering particles in the sheath or catheter. Given that an OCT probe has a rotatable fiber disposed in one or more sheaths, such sheaths can be doped with one (see FIGS. 2A-3D and as otherwise described herein) or more layers (or sublayers) (see FIG. 2B). A dopant layer on or in the sheath can be selected to reduce unwanted reflections while being detectable by software as a calibration feature.

Detection of One or More Calibration Features

Various calibration features can be used for a given intravascular data collection probe. In one embodiment, the calibration feature can include a doped sheath that is selectively doped with scattering particles. The sheath is a type of elongate substantially curved cover having an optical fiber disposed therein. Such a sheath typically has an elliptical cross section which includes a circular cross-section. In one embodiment, the software can be configured to identify a given catheter based on its components or calibration features. In addition, the software performs various filtering, detecting, and thresholding steps to identify the sheath such as by a particular pattern or other characteristic on each frame. Various constraints and prior knowledge of the design of a given calibration element can be used to identify it. A filter can include a stepwise function with notches sized to pick up elements along a scan line such as a thickness of doped region. A given filter can be represented as a matrix or other operator.

Figure 6A:
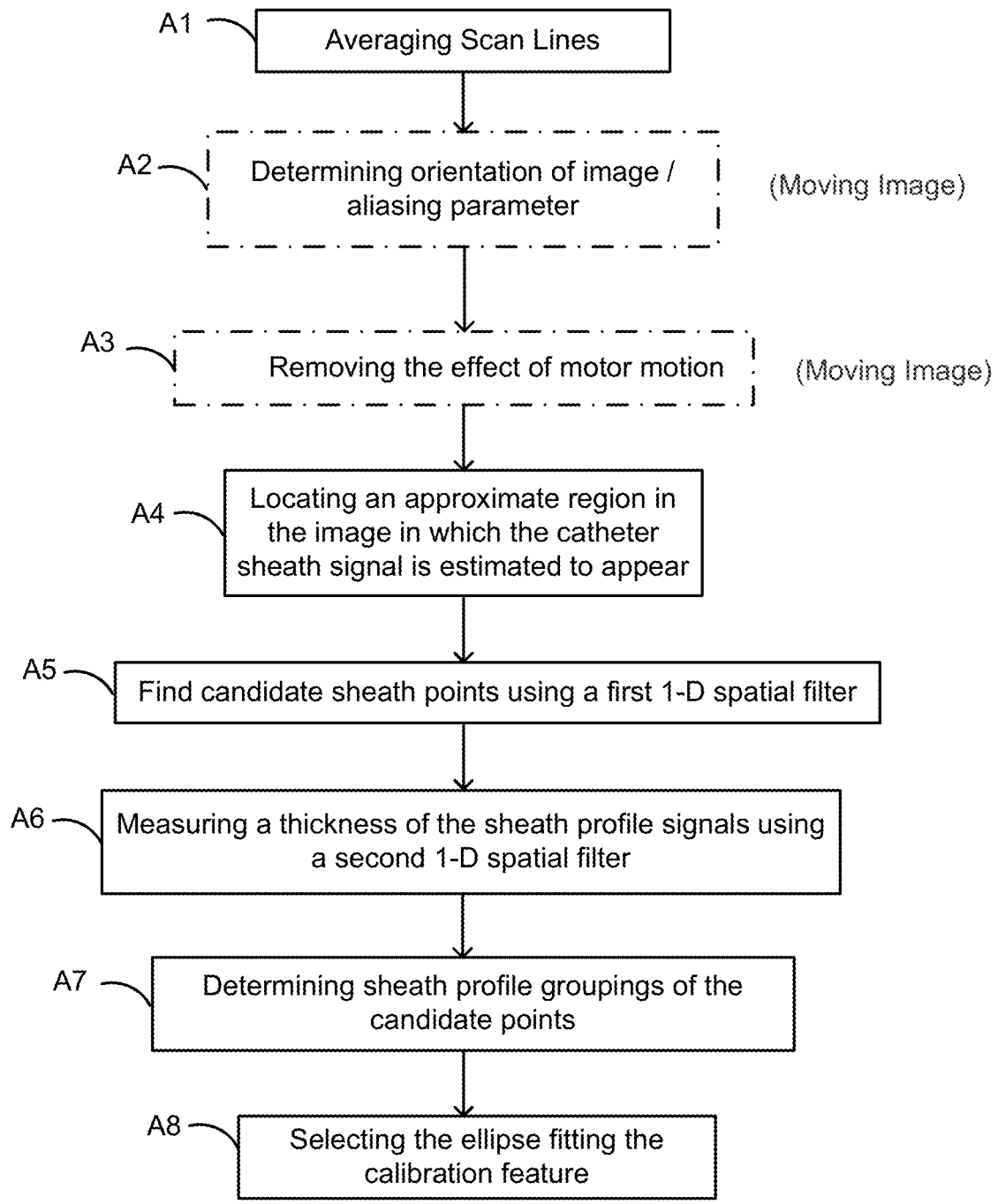
FIG. 6A is a flow chart reciting various steps suitable for tracking or analyzing a calibration feature such as doped sheath in frames of optical coherence tomography data according to an illustrative embodiment of the invention.

Various steps for locating a calibration feature such as a intense region in the image, a border or interface, an annular region, an irregular shape or other suitable features in an OCT image are described in FIG. 6A. In one embodiment, the software and systems described herein use various processing steps (Steps A1-A8) and software modules to identify a doped sheath. Various physical constraints can be to facilitate its detection in an OCT frame. The doped sheath is typically circular or elliptical. The sheath can deform and twist in a vessel although its overall area or perimeter should not change across frames. The doped sheath is generally not disposed in the center of the blood vessel, but rather can move around in various non-concentric positions. These geometric limitation can be used to estimate areas where the sheath appears.

Figure 6B:
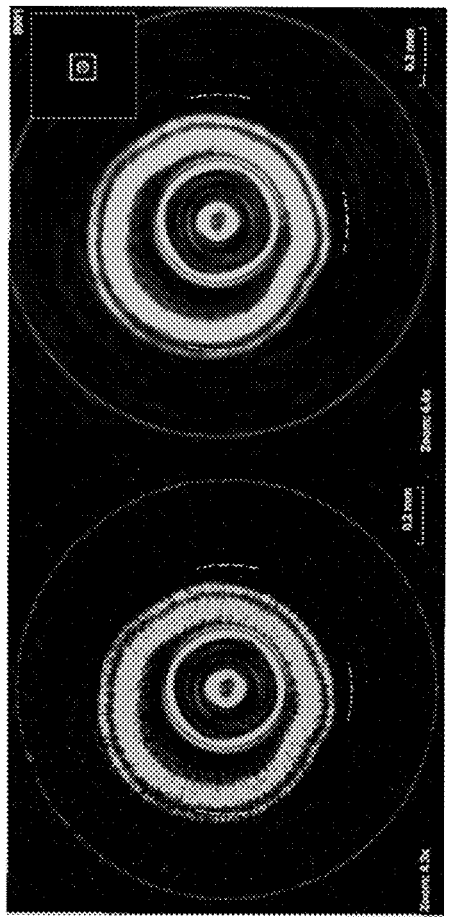
FIG. 6B is two versions of an image depicting a cross-sectional view of a blood vessel obtained using optical coherence tomography in which one version has undergone line averaging and the other version has not according to an illustrative embodiment of the invention.
Figure 6C:
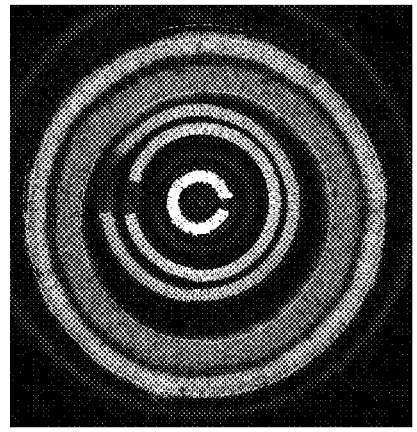
FIG. 6C is an image of a cross-section of an optical coherence tomography image showing a blood vessel with various regions including a doped sheath being identified with a graphical overlay.

Further, the thickness of the doped sheath can vary based upon manufacturing tolerances. In addition, the dope sheath is susceptible to speckle as shown by the dark regions in the left side of FIG. 6B in contrast with the version shown to the right in which line averaging has been performed. All of these factors present challenges to tracking the doped sheath as a calibration feature.

In one embodiment, detecting a calibration feature can be found using the methods and concepts described herein. Steps A1-A8 can be used on or more times to identify a given calibration feature. Filters can be used together or separately in one embodiment. The steps include averaging scan lines A1, locating an approximate region in the image in which the catheter sheath signal is estimated to appear A4, finding candidate sheath points using one or more filters such as a 1-D filter kernel A5, measuring a thickness of the circular or elliptical signals using a second filter such a 1-D spatial filter A6, determining circular; likely off-center, groupings of the candidate points A8, and selecting an ellipse A8. In the case when the images are moving steps A2 and A3 can also be performed.

In one embodiment, a first filter is used. The first filter can be configured to work in various possible case (in-vivo/ex-vivo and across the entire doped layer thickness). Preferably, the filter is selected to deal with the scenarios that the probe and the calibration feature will be exposed to in use. In one embodiment, one or more filters are configured to address the following circumstances or parameters:

Doped region/or other feature having a thickness: specifications for the thickness of calibration feature is 0.0015"+/−0.0005". As a result, a minimum thickness 0.0010" (25 um) is used.

Clear region: OCT resolution cell thickness of 20 uM is used in one embodiment.

Mismatch region: Zero. Optical index mismatch may (ex-vivo in air) or may not (in-vivo in contrast) be present.

For the second filter, multiple filtering operations are performed one or more times:

Doped region/or other feature having a thickness: Varied specifications for the thickness is (25-50 uM)

Clear region: Varied inversely with the doped layer thickness (Total sheath thickness is constant)

Mismatch region: Zero. Optical index mismatch may (ex-vivo in air) or may not (in-vivo in contrast) be present.

In one embodiment, if a doped sheath is not found, such as would be present in FIGS. 2B, 3A and 3B, the system or a calibration module tries to search for a doped sheath or ring next to the fiber 3 such as would be present in FIG. 2A. The lack of a doped sheath can be an indication that a different type of catheter is being used, but is not determinative. If the system cannot find a doped layer or ring near the fiber, an error signal is generated. If this system finds and loses or cannot find a calibration feature it can mark the data as unusable or generate an operator alert.

Catheter Types and Features

FIG. 2A depicts one catheter type and FIGS. 2C and 2D depict show various features of two catheter types. The system is configured to identify these types and others. Typically, the system looks for a doped sheath first and absent finding that looks or a doped ring near the fiber. This is performed as part of the auto calibrate before a pullback is performed. In this way, catheter type informs how data can be processed in the modular image processing pipeline.

The catheters are designed to work with a flush solution which fills the region between the fiber and the sheath. This helps prevent blood ingress and is used to flush a lumen for OCT imaging during a pullback. The solution is configured to provide a suitable level of index matching between the fiber and the sheath. When the probe is in air, the doped sheath is easier to locate relative to when it is in blood. The doped sheath resembles tissue to a greater degree when compared to a PET ring near the fiber. As a result, multi-threshold sampling can be performed to identify candidates for the doped sheath. These can be scored and when a sufficient number of samples indicate a suitable probability that a dope sheath exists, that sheath position is used for a given frame.

Multiple Prefetch Architecture Embodiment Features

Figure 7:
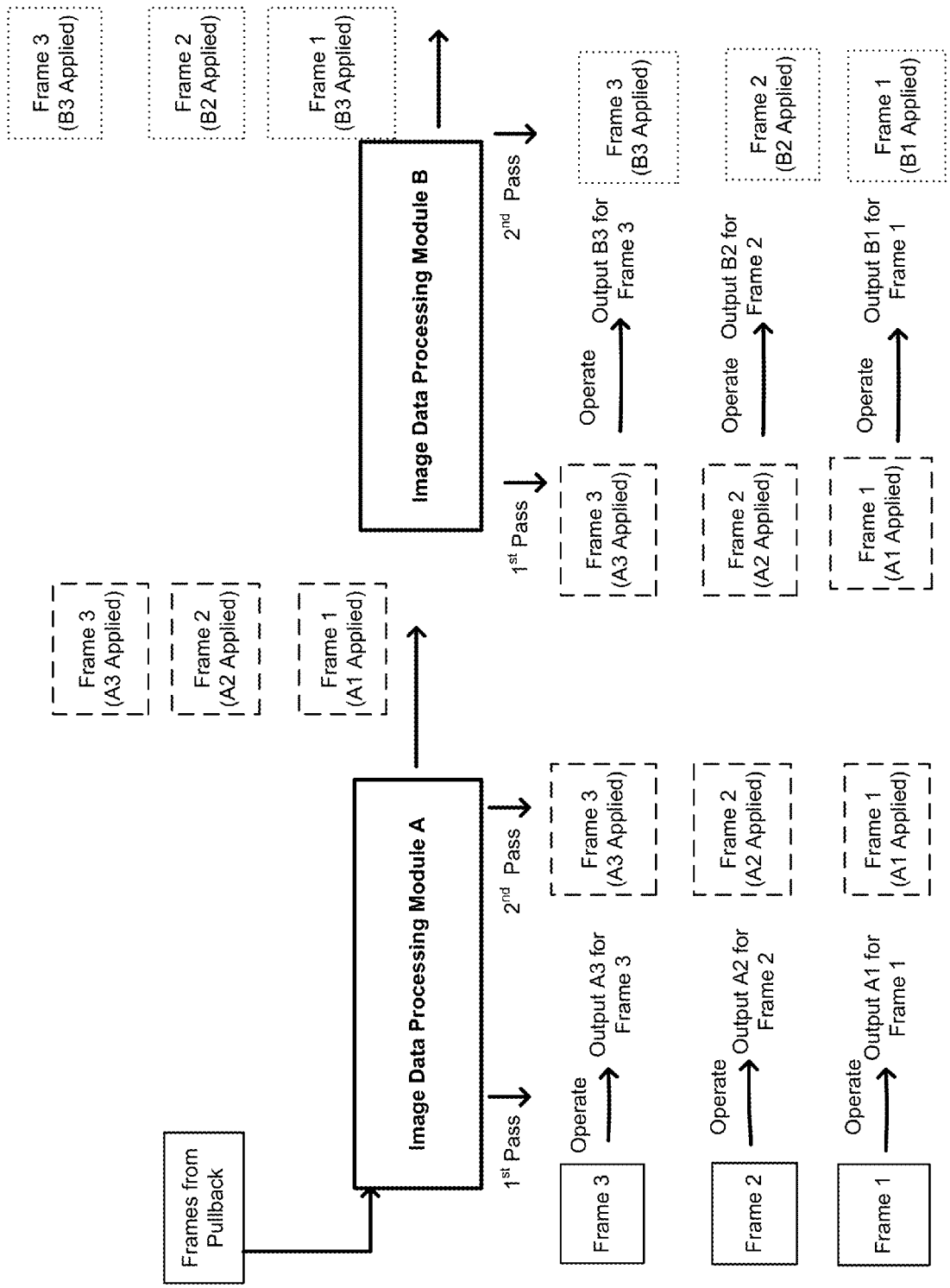
FIG. 7 is a schematic diagram of a image data processing module configured to direct the processing of image data relative to a software modules described herein such as, for example, the modules in the processing pipeline paths of FIG. 8.

FIG. 7 depicts an image data processing architecture suitable for processing scan lines, samples or frames obtained using an intravascular imaging probe. Initially frames from the pullback of the probe are provided as an input for first image data processing module, shown here in FIG. 7 as image data processing module A. In general, the steps and processes described herein can be configured to operate at the sample, the scan line, the frame, or the set of frames level in a given embodiment. As a result, reference to one of the foregoing types of OCT data can be changed to another of the types of OCT herein without limitation. Thus, a reference to a frame also contemplates the relevant embodiment operating on a scan line and vice versa. In one preferred embodiment, all of the calibration, processing, and filtering steps described herein are performed with respect to scan lines.

In one embodiment, the image data processing module is configured to operate on frames from the pullback such as Frame 1, Frame 2 and Frame 3 shown. Each frame is received by the image processing module A as part of the first pass during which module operates on each frame and generates an output for each frame. For Frame 1 the output is output A1 for Frame 1, for Frame 2 the output is output A2 for Frame 2, and for Frame 3 the output is A3 for Frame 3.

In one embodiment, each of the outputs can be a value such as a possible value used to shift pixels in a frame or sample in scan line consistent with making a sample path and reference path length substantially the same or aligning or detecting a calibration feature in different frames or scan lines. The outputs can be operators themselves such as matrices for application to other frames and other image processing modules. In one embodiment module A is one of the modules shown in FIG. 8 and module B, is another module from FIG. 8. In one embodiment the first pass performed with respect to module A is a prefetch.

In one embodiment, image processing module A receives a frame or a plurality of scan lines from a pullback and processes the frames or scan lines generates frame or scan line outputs. The second pass can be the application of the output such as output A3 applied to Frame 3 shown in the second pass, with dotted frames. Given the sequential arrangement of module A proceeding module B, as shown in the top middle portion of FIG. 7, Frames 1, 2 and 3 having been processed by module A resulting in dotted boxes shown in Frame 1 (A1 applied), Frame 2 (A-2 applied), and Frame 3 (A3 applied).

These process frames are then provided in image data processing module B and each frame is operated upon as shown as part of a first pass such that outputs B1, B2, and B3 are generated. As shown, these outputs are applied to the input frames to module B such that the resulting frames are Frame 1 with B1 applied, Frame 2 with B2 applied, and Frame 3 with B3 applied. Although the reference to A3, A2, and A1 is not maintained, the operation applied by module A carries through to the output frames by module B shown in the top right corner of FIG. 7 unless, for example, module B is configured to undo some or all of the operations of the module A.

For example, in one embodiment module A may be configured to provide continuous calibration on a set of frames received from a pullback. As a result, following the application of module A, the frames would be calibrated. Further, module B would advantageously receive calibrated frames prior to the application of any additional image processing, such as, for example, shadow removal lightening or guide wire detection. Various post pullback processing frames shown in FIG. 5 and the processing module shown in FIG. 8, as well as any other software modules described herein, are suitable for use with the architecture depicted and described with regard to FIG. 7 in any equivalents or extensions thereof.

Multi-Frame Pipeline and Sequential/Order Frame Processing

In part, one embodiment of the invention relates to a multiple prefetch architecture. For example, in one embodiment calibration results are computed with regard to a first prefetch of frames of image data to be displayed or processed by a second prefetch of frames of image data. In one embodiment, raw unprocessed image data can be displayed from a pullback as a second stream of image data is processed according to the image processing pipeline described herein.

As an example of the use of multi-frame data, during lumen detection, the use of two frames helps to increase the accuracy of detecting the lumen boundary. For example, a guidewire casts a shadow obscuring part of the boundary. However, a scan line can also be blocked by uncleared debris or blood in the lumen as shown. As a result, the scan line may image multiple points of occlusion. However, this debris tends to be small, and hence, by looking at previous frames, the software can be used to determine that because the wall has continuity between frames, while the debris will not, debris can be distinguished from wall.

Performing two passes on image data frames allows all of the operations of a give module, such as module A in FIG. 7 to be performed and cached. These can be kept as an array or applied to the set of frames from the pullback. The set of modified frames or frames and such an array can then be passed to subsequent image data processing pipeline module, such as module B. In one embodiment, module A and module B can be any of the software modules selected from image processing software pipelines shown in FIG. 8. In one embodiment, the prefetching of data for one image data processing module from either a set of images obtained from an imaged data collection pullback, whether OCT, IVUS, or otherwise can be used as inputs to one or more of the processing paths of FIG. 8. In one embodiment, one or more of the paths spanning FIG. 8 can be selected based on processing resources and the outputs of interest to a user.

Given that the pullback causes lumen motion, beginning the image processing pipeline with continuous calibration and ending with lumen detection following a pullback is preferred. In one embodiment, continuous calibration refers to a software-based calibration by which the catheter or optical fiber in each frame is aligned between frames. Although, once lumen detection has been performed, one could select the previous step to be any of those mentioned for use in a multi-frame system.

Figure 8:
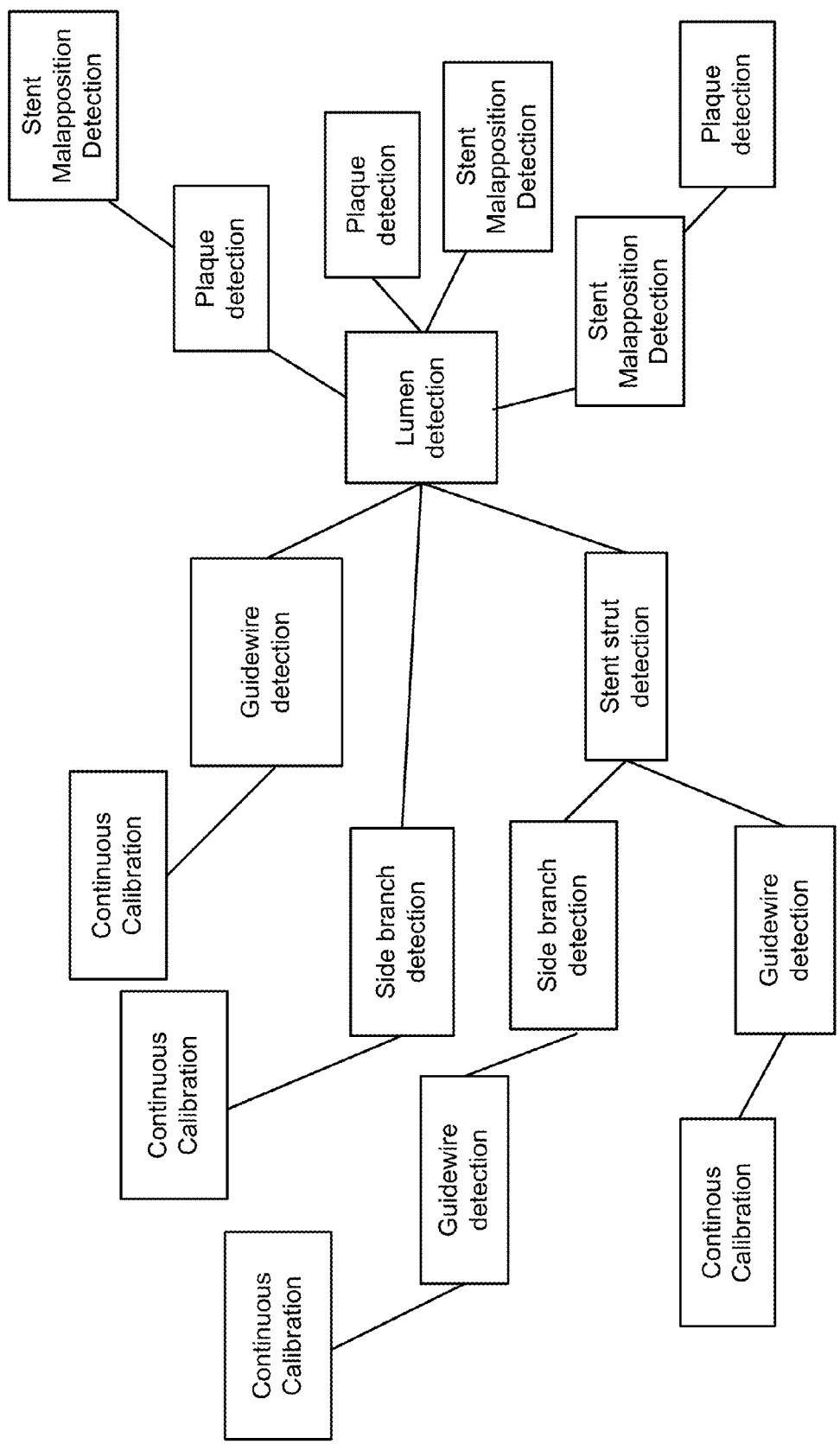
FIG. 8 is an arrangement of image processing software modules along different processing pathways based upon physiological and other considerations to improve the results of the application of such modules.

In this way the pipeline software modules are arranged in a tree structure based on physiological and data processing constraints as shown in FIG. 8. The physiology and data input can lead to a preferred order for modules in the pipeline. In some instances, the order improves results or makes certain outputs possible, such as lumen detection. The selection of the order of swappable encapsulated software modules and the benefits of continuous calibration lead to improved data processing results and efficiencies.

As shown in FIG. 8, the software modules can be configured to be swappable and are configured to be encapsulated relative to each other to reduce the likelihood of error propagation and to enable swapping of modules and changes to processing order for frames. Stages of the image data pipeline are sequenced to improve resolution and avoid errors based on physiological constraints and a multi-stage calibration routine. In one embodiment, the algorithm has two phases. The first phase runs during a prefetch to collect potential guide wire regions, while, the second phase is executed if the pullback has multiple frames. The first phase runs as a single frame process, which gathers information for each frame. The second phase is executed as a multiple frame process, which uses the information from single frame process in one embodiment.

The multi-frame system uses two or more passes to improve accuracy and reduce noise. One pass operates on and analyzes frames and generates corrective values or other outputs based on module operating. Calibration is selected as first image data processing module. The first pass through the calibration module identifies radial or other distances by which the image needs to be shifted to align optical fiber received signal between frames. Lumen detection is later in the pipeline because it is dependent on guidewire detection, side branch detection, and stent strut detection happening before it in the pipeline, in one embodiment.

Resolving Image Features Using Low Intensity Regions and Other Structural Features In FIG. 9A a portion of an intravascular imaging probe is shown. The probe includes a beam director 180 that is adjacent to a section of optical fiber 190 that includes a glass section. Two fusion splices further in the probe can create a low intensity region as shown by the irregular region in the lower section of FIG. 9A. Since this region corresponds to a section of glass, light should pass through without excessive scattering.

One challenge associated with OCT and imaging probes is that rings can easily form in an image as a result of the probe's substantially circular cross-section and many components. Rings of this nature, which can be produced by catheters, splices and other optical components of an imaging system, can interfere with calibration. For example, such rings can be locked on and erroneously processed as a calibration feature.

In one embodiment, known intensity regions such as the splice region shown, and other regions in the image can be used to exclude certain signals, such as rings, as candidates for a calibration feature, when such features are being sought after. Thus, a known low intensity region in an image frame, based on probe components and their arrangement, can be used to improve calibration efficiency and exclude erroneous rings and other artifacts.

FIG. 9B shows a manufacturing problem that causes a related imaging artifact. The optical fiber 195 shown is disposed in a layer that is adhered to the fiber. This is in contrast with a calibration feature in the imaging field with respect to which a probe can move relative to in a given embodiment. The off-center placement of the fiber can lead to additional calibration steps. Since distance X and Y differ, when rotating, the distances recorded as scan lines are off by an amount that can skew results and impact subsequent image processing. As a result, other calibrations features can be used to compensate for this result.

Continuous Calibration and Operational Triggers

Figure 10B:
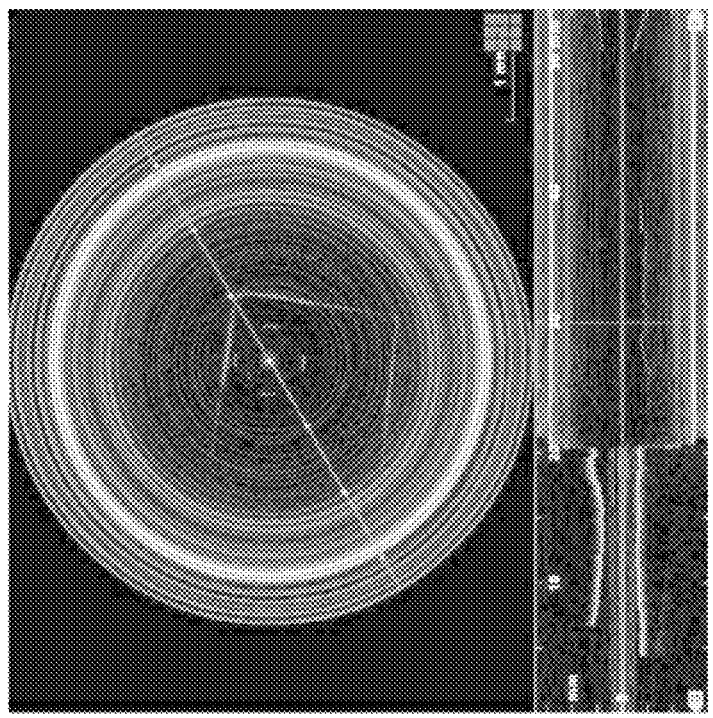
FIGS. 10A-10B are cross-sectional and longitudinal mode views of an OCT generate image depicting error states that can be monitored for an identified in response to a loss of lock or deviation detected by a calibration software module according to an illustrative embodiment of the invention.
Figure 10A:
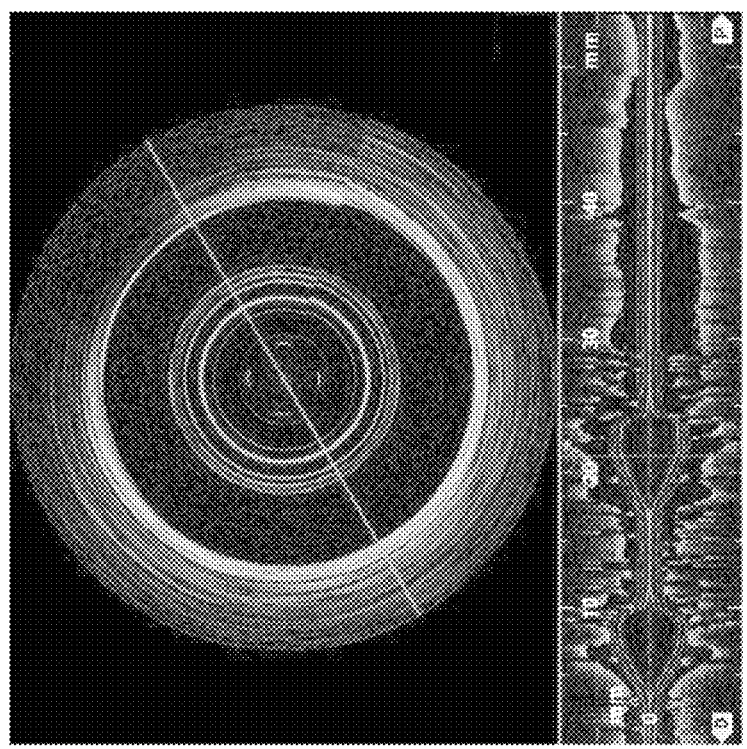

In general, motor based calibration approaches do not detect deviations in a normal operating mode of an imaging catheter. In FIG. 10A, the imaging probe is not operating properly as can be seen from the periodically expanding pattern in the L-mode in the bottom portion of the figure. Similarly, the L-mode in FIG. 10B indicates that the fiber or lens is no longer relaying a signal. The continuous calibration features described herein can include a periodic tracking of cross-sectional images. As a result, by using such cross-sectional images, which can include a calibration feature, a loss of lock on a calibration feature during a given calibration feature can be used to stop an imaging procedure or to otherwise alert an operator. A loss of lock or tracking with respect to a calibration feature can trigger an alert or inform an operator that the pullback data cannot be used. The threshold can include a loss of lock over a predetermined number of frames or a predetermined time period.

Cross Frame Data Fitting, Interpolation, and Spline-Based Software Embodiments

As described herein, a set of frames of image data are generated based upon optical signals sent and received by an optical coherence tomography data collection probe. The probe includes a probe tip which includes or is in optical communication with an optical fiber.

The probe is pulled back through the blood vessel as it rotates such that the beam of light sent to the vessel wall from the probe tip traces a spiral as it moves along the section of the blood vessel being imaged. This section has a specified pullback distance D. A set of frames are obtained with regard to the pullback distance D.

With respect to some of the frames, errors may result that cause a particular frame to be unusable. For example, as described herein, an ellipse can be fit to a doped layer disposed relative to the sheath such as in or within or exterior to the sheath. This doped layer is used for various purposes such as different calibration routines. If such an ellipse fitting fails, or if the resulting ellipse fit is computed erroneously relative to the location of the doped layer, the resulting fit can be considered discarded or ignored during subsequent calibration processing steps.

The polymer sheath in which the probe is disposed during the pullback generally has an elliptical cross-section. The optical fiber of the probe and the sheath are visible or detectable in frames of image data. As a special case of such an ellipse, this cross-section is circular. Given the movement of the artery and the flexible nature of the sheath, the sheath can be curved or folded such that from a cross-sectional perspective the perimeter of the sheath ranges over various regular or irregular continuous curves. Given that the sheath is a physical object various parameters such as the perimeter of a given sheath should be the same or substantially the same across frames obtained along the pullback distance. As a result, even if the sheath deforms from an ellipse to an irregular contour the perimeter should be constant or substantially constant between frames.

In one embodiment, the perimeter is currently being estimated based on the best fit ellipse. In another embodiments compute the perimeter directly from the computed offsets and this might be more accurate, although it might be more prone to noise in certain circumstances. In one embodiment, the mean diameter of the sheath can be used as another metric which should generally remain constant between frames. The position of the optical fiber can also be tracked across frames. In one embodiment, one or more calibration software modules are used to perform the spline-based or elliptical fitting described herein. The software modules can be configured to include constraints to prevent discontinuities and jumps between frames.

Various other parameters can be tracked including without limitation: eccentricity of ellipse, center position of ellipse, perimeter of ellipse, and perimeter of offsets. Eccentricity of ellipse—if eccentricity varies wildly from one frame to a next, that could indicate an error in ellipse fit and thus be an outlier. In one embodiment, perimeter of offsets is potentially more accurate as a calibration metric than perimeter of ellipse, but this could also be subject to errors based on false offset detections that are essentially ignored by ellipse fit.

Figure 11:
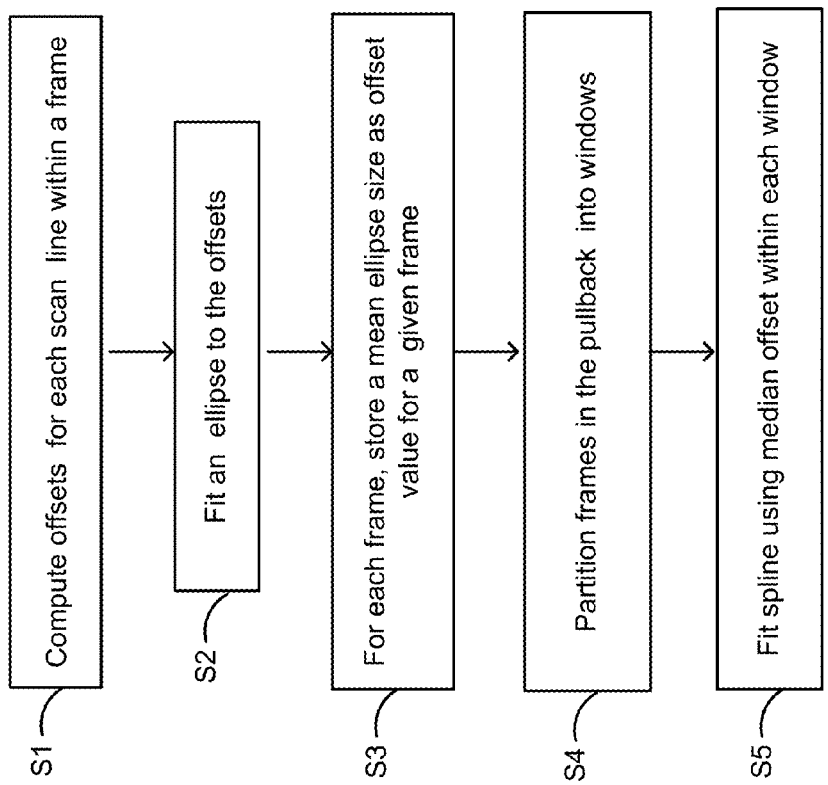
FIG. 11 is a flow chart of a curve fitting process suitable for interpolating or calibrating between a plurality of OCT frames according to an embodiment of the invention.

In general, if an ellipse can be fit to the sheath or scattering particles disposed therein for a given frame, the frame is likely to be useful for calibration and imaging. This elliptical fitting is used as part of one or more calibration routines. In one embodiment, such elliptical fitting on spline-based fitting is performed using one or more steps as outlined in FIG. 11.

Offsets are computed for each line within a frame, the ellipse is fit to the offsets. For each frame, a size value for the ellipse such as a mean diameter or mean radius of the ellipse is saved as an offset value for a given frame. All frames in the pullback are partitioned into 1 mm discrete windows. The median offset within each window, based on the per frame offset values, is used as the value for fitting the spline.

The spline effectively models the offset for all frames, and due to the median being used on each window, outlier offsets are effectively ignored. Because the spline fit will be smooth, it is a suitable value to use for calibration. The spline does not select frames to be displayed. The spline does effectively interpolate offset values for frames on which the offset detection failed or for which the detected offset was computed erroneously (an outlier).

In general, features which can be tracked for consistency across frames such as a locus for possible fiber core positions, sheath diameter, sheath perimeter, and other factors outlined herein can be used to generate a relationship for interpolating across frames. This is useful in cases where the sheath detection or elliptical fit fail. When such an error occurs, a polynomial spline or other interpolation method can be used to obtain calibration correction values for the frames that had the error condition. Specifically, interpolation refers to the process of extracting suitable calibration correction values for frames on which offsets could not be computed by using the valid offsets from surrounding frames in which the offsets are computed correctly.

There are several error conditions that would render the spline fit unusable. In one embodiment, processing of frames using a polynomial fit or spline fit based method terminates or is otherwise is aborted if one or more of the following conditions apply:

The computed difference between median offset from one window to the next exceeds a threshold (about 20 microns)

A median value for any of the windows cannot be found. This occurs if no frame within the window has a valid offset measurement.

Over ½ of all frames have no valid computed mean diameter (offset).

In one embodiment, the data fitting of frame of image data is performed using a spline or spline fitting based method. In one embodiment, the inputs of the data fitting algorithm for continuous calibration are inputs are the median offset values computed on each 1 mm window in the pullback. The parameters are the median offset values computed in each window of size 1 mm along the pullback. Performing a polynomial fit relative to a set of values obtained for the different windows that is representative of the ellipse such as its size or position is used to test the likelihood that the ellipse has been found. If the fit of the ellipse parameter is consistent over the windows, this supports the position that the correct feature has been identified in each image frame.

The fitting process performs a fit with regard to the offset values such as an ellipse size value or parameter that are computed for each frame. If spline algorithm or continuous calibration otherwise does not work for a particular reason, the software is configured to direct the user to the manual verification/adjustment screen. The probe image is provided to the user for manual selection or to provide a set of candidates for the user to evaluate or request more information from the user.

Data Collection Probe Embodiments and Parameters

In one embodiment, an inner layer, a middle layer, or an outer layer of the probe can be doped. In one embodiment, two closely-spaced layers are used to provide a double-line reflection. These double layers can be disposed in the sheath or outer layer of the probe in one embodiment. The double-line reflection configuration can be used to mitigate spurious reflections.

In one embodiment, a data collection probe can include two layers having a space in between the doped material in separate components, rather than two layers within the same component. For example, a combination of components with either full-wall thickness of doped material (such as a PET layer around near the optical fiber) or doped layer(s) (such as the window tubing with doped inner-layer). A combination of doped rings can be used in such a manner, for example: doped lens PET and doped window tubing—each with doped full-wall (not layered), or one or both with a doped layer(s) can be used for some data collection probe embodiments.

In one embodiment, the flexible sheath through which light passes to and from the probe tip is made from a thermoplastic material. An example of such a material is a polyether-polyamide block co-polymer. A partially doped sheath can be achieved using various plastic materials that can be formed or molded into a tube or other shape.

In one embodiment, the doped layer is disposed within the sheath and has a thickness that ranges from about 0.001 inches to about 0.004 inches. In one embodiment, a substantially scattering particle free layer is disposed within the sheath and has a thickness that ranges from 0 to about 0.004 inches.

In one embodiment, the invention relates to an optical coherence tomography probe. The probe includes a substantially transparent curved cover defining a first bore and comprising a polymer, the substantially transparent curved cover comprising a substantially elliptical cross section comprising a first annular region having a first annular thickness T1 and a second annular region, the second annular region doped with a light scattering material and having a second annular thickness T2, the first annular region substantially free of the light scattering material; a beam director; a torque wire defining a second bore; a rotatable optical fiber in optical communication with the beam director, the rotatable optical fiber disposed in the second bore, the torque wire slidably disposed within the first bore.

Pixel and Clear Layer Parameters for Sheath for Intravascular Probe

Figure 12:
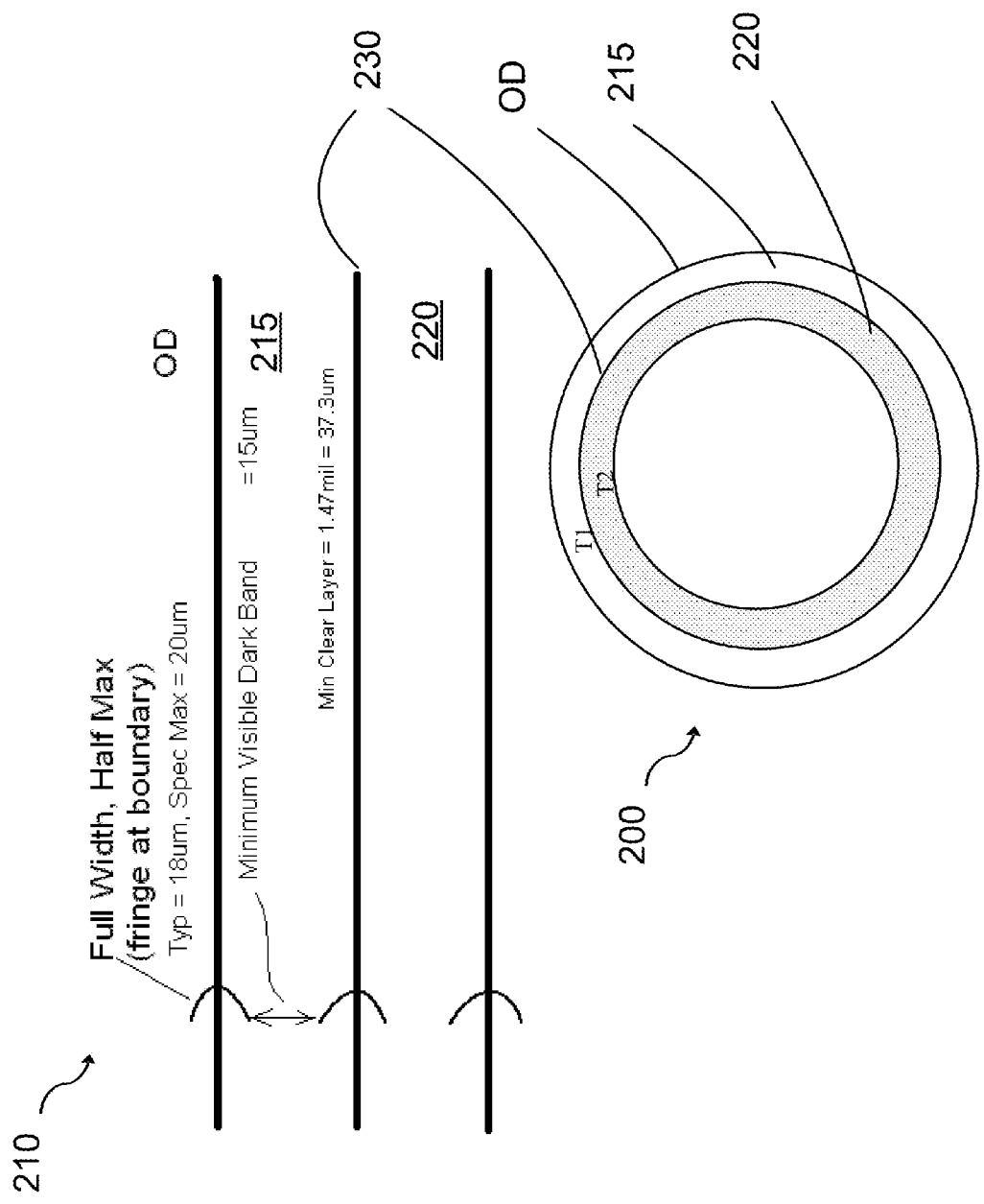
FIG. 12 is a schematic diagram showing a doped sheath and a magnified view of its layers and OCT signal changes based on the thickness of such layers according to an illustrative embodiment of the invention.

As shown in FIG. 12, an exemplary sheath 200 is illustrates a magnified view 210 of various interface layers for the sheath 200. The interface layers include the outer layer or outer diameter of the sheath identified as OD. One layer 215 of sheath 200 is substantially free of light scattering particles as a dopant and has a thickness T1. One layer 220 of sheath 200 includes light scattering particles as a dopant and has a thickness T2.

In one embodiment, the doped sheath used for a particular calibration feature is adjusted to account for OCT resolution. The OCT resolution cell in the sheath 200 is smaller (better) than the resolution in air by l/n-material, where n-material is the index of refraction of the material. In one embodiment, the sheath 200 is a polymer, and most polymers have an index of ~1.5. As a result, 8-20 um resolution in air is a ~12.5 um resolution cell in the polymer of the sheath 200.

In one embodiment, the clear layer, layer 215, appears thinner by one resolution cell than actual while the doped layer 210 appears thicker by one resolution cell than actual under OCT. The resolution issues resulting from the use of OCT can be evaluating using two equations as follows:

$$DLT+1*RCm=CLT-1*RCm \text{ (desired condition of equal apparent thickness)} \quad (1)$$

Where CLT=clear layer thickness, DLT=doped layer thickness, RCm=Resolution Cell, material and $$DLT+CLT=TT, TT=\text{total sheath wall thickness} \quad (2)$$

As an example, for a 100 um window thickness (actual), the doped layer is 37.5 um and clear layer is 62.5 um (actual), RCm=~12.5 um. This yields the desired ratio of 1:1, apparent layer thicknesses. (37.5+12.5=62.5−12.5). The build ratio for the two layers of the sheath is then 3:5 for this TT and RCm. [37.5:62.5=3:5, where 3:5 is expressed in units of RCm—the minimum quanta for detection.

As a result, the minimum sheath wall is when CLT−1*RCm=1RCm, so CLT=2*RCm, or 25 um. Then the minimum sheath wall thickness is 37.5 um and the DLT is 12.5 um. In this case the build ratio is 1:2. This assumes the minimum detectable thickness is just 1 RCm.

Speckle reduction can reduce the uncertainly on the apparent wall thickness by 1/sqrt(n), where n is the number of sampled lines. So RCm can go down by 1/sqrt(n). In our case, we can average 8 lines [(spot size*number of lines per cross section)/circumference=8], so RCm, avg becomes 4.4 um.

In one embodiment, the ratio of T1 and T2 ranges from greater than about zero to 1. In one embodiment, the boundary between the DS and UDS regions is a calibration feature. In one embodiment, the ratio of T2 to T1 is about 1:5. In one embodiment, the ratio of T2 to T1 is about 3:5. In one embodiment, the ratio of T2 to T1 is about 4:6.

In one embodiment, the thickness of the sheath 200 is T1+T2. In one embodiment, T1+T2 is about 60 μm. In one embodiment, T1+T2 is about 100 μm. In one embodiment, T 1+T2 is about 120 μm. In one embodiment, T1+T2 is about 140 μm. In one embodiment, T1+T2 is about 160 μm. In one embodiment, T1+T2 is about 180 μm. In one embodiment, T1+T2 is about 200 μm. In one embodiment, the light scattering material comprises titanium dioxide.

In one embodiment, the calibration feature includes an arrangement of light scattering particles that are sized and positioned such that single scattering is maintained with respect to incident light. Thus, in one embodiment a multiple scattering threshold is set as constraint when disposing scattering particles in a given elongate layer or film of a data collection probe. This follows because attenuation will increase rapidly while return signal (doped layer brightness) will not increase as much.

In the description, the invention is discussed in the context of optical coherence tomography; however, these embodiments are not intended to be limiting and those skilled in the art will appreciate that the invention can also be used for other imaging and diagnostic modalities or optical systems in general.

The terms light and electromagnetic radiation are used interchangeably herein such that each term includes all wavelength (and frequency) ranges and individual wavelengths (and frequencies) in the electromagnetic spectrum. Similarly, the terms device and apparatus are also used interchangeably. In part, embodiments of the invention relate to or include, without limitation: sources of electromagnetic radiation and components thereof; systems, subsystems, and apparatuses that include such sources; mechanical, optical, electrical and other suitable devices that can be used as part of or in communication with the foregoing; and methods relating to each of the forgoing. Accordingly, a source of electromagnetic radiation can include any apparatus, matter, system, or combination of devices that emits, re-emits, transmits, radiates or otherwise generates light of one or more wavelengths or frequencies.

One example of a source of electromagnetic radiation is a laser. A laser is a device or system that produces or amplifies light by the process of stimulated emission of radiation. Although the types and variations in laser design are too extensive to recite and continue to evolve, some non-limiting examples of lasers suitable for use in embodiments of the invention can include tunable lasers (sometimes referred to as swept source lasers), superluminescent diodes, laser diodes, semiconductor lasers, mode-locked lasers, gas lasers, fiber lasers, solid-state lasers, waveguide lasers, laser amplifiers (sometimes referred to as optical amplifiers), laser oscillators, and amplified spontaneous emission lasers (sometimes referred to as mirrorless lasers or superradiant lasers).

Non-Limiting Software Features and Embodiments

The following description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic device, network PCs, minicomputers, mainframe computers, and the like. The invention can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "detecting" or "measuring" or "calculating" or "comparing" "fitting" or "interpolating" or "applying" or "thresholding" or "filtering" or "calibrating" or "generating" or "determining" or "displaying," or Boolean logic or other set related operations or the like, refer to the action and processes of a computing device, or electronic device, that manipulates and transforms data represented as physical (electronic) quantities within the computer system's or electronic devices' registers and memories into other data similarly represented as physical quantities within electronic memories or registers or other such information storage, transmission or display devices.

The present invention, in some embodiments, also relates to apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

Embodiments of the invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating one or more or prefetches, calibration corrections, offsets, detecting lumen borders, comparing measured perpendicular distances relative to set thresholds, and otherwise performing image comparison, thresholding, signal processing, pattern matching, artifact removal, continuous calibration, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, kernel filters, filters, thresholding, pattern matching, interferometer signal data, guide wire locations, shadow region locations, side branch locations, side branch diameters, intensity profiles, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

What is claimed is:

1. A method of detecting a calibration feature disposed in a vessel having a vessel wall, the vessel scanned using an intravascular imaging probe, the method comprising:
   storing image data obtained during a pullback through the vessel in a memory device, the image data comprising a plurality of frames, each frame comprising scan lines;
   averaging scan lines for a first frame of the plurality of frames to obtain a speckle reduced first frame;
   identifying a region in the speckle reduced first frame in which the calibration feature is estimated to appear;
   identifying candidate samples of the calibration feature;
   identifying a region defined by the candidate samples using a thickness of at least a portion of the calibration feature; and
   fitting a curve to the candidate samples to define a boundary of the calibration feature in the speckle reduced first frame.

2. The method of claim 1 wherein the intravascular imaging probe comprises an optical fiber and a beam director in optical communication with the optical fiber.

3. The method of claim 2 wherein the calibration feature is a substantially elliptical cross-section of substantially transparent curved cover comprising a polymer, wherein the elliptical cross section comprises a first annular region and a second annular region, the second annular region doped with a light scattering material.

4. The method of claim 2 further comprising rotating the optical fiber and the beam director within the calibration feature and generating an image of a cross-section of the blood vessel, the image comprising a first annular region having a first optical intensity and a second annular region having a second optical intensity, the second optical intensity brighter than the first optical intensity.

5. The method of claim 3 wherein the thickness is an annular thickness of the second annular region and wherein the second annular region is disposed concentrically within the first annular region.

6. The method of claim 3 further comprising
   averaging scan lines for a second frame of the plurality of frames to obtain a speckle reduced second frame;
   identifying a region in the speckle reduced second frame in which the calibration feature is estimated to appear;
   identifying candidate samples of the calibration feature using a first spatial filter;

identifying a region defined by the candidate samples using a second spatial filter having a thickness of at least a portion of the calibration feature; and fitting a curve to the candidate samples to define a boundary of the calibration feature in the speckle reduced second frame.

7. The method of claim 5 further comprising receiving the thickness from a device attached to the intravascular imaging probe.

8. The method of claim 7 further comprising searching for the second annular region using the thickness.

9. The method of claim 1 further comprising
identifying a dark region having a first intensity in one or more of the scan lines of a frame; and excluding optical signals having a second intensity appearing in the dark region if the second intensity is greater than the first intensity.

10. The method of claim 1 further comprising wherein one or more of the identifying steps are performed using one or more filters.

11. The method of claim 1 further comprising rejecting image data associated with the boundary of the calibration feature, when a shape of the boundary is irregular or exceeds a shape threshold.

* * * * *